US008974387B2

(12) United States Patent
Shadforth et al.

(10) Patent No.: US 8,974,387 B2
(45) Date of Patent: Mar. 10, 2015

(54) ANALYTE TESTING METHOD AND DEVICE FOR DIABETES MANAGEMENT

(75) Inventors: Ian Shadforth, San Francisco, CA (US); David Price, Pleasanton, CA (US); Gretchen Anderson, Oakland, CA (US); Lorraine Comstock, Saratoga, CA (US); Mary McEvoy, Belmont, CA (US); Douglas Graham, Moray (GB); Alexander Strachan, Moray (GB); Alistair Longmuir, Forres (GB); Robert Cavaye, Penarth (GB); Gillian Teft, Maryburgh (GB)

(73) Assignee: LifeScan Scotland Limited, Inverness (GB)

( * ) Notice: Subject to any disclaimer, the term of this patent is extended or adjusted under 35 U.S.C. 154(b) by 706 days.

(21) Appl. No.: 12/826,674

(22) Filed: Jun. 30, 2010

(65) Prior Publication Data
US 2011/0077493 A1 Mar. 31, 2011

Related U.S. Application Data

(60) Provisional application No. 61/246,630, filed on Sep. 29, 2009.

(51) Int. Cl.
*A61B 5/00* (2006.01)
*A61B 5/145* (2006.01)
*G06F 19/00* (2011.01)

(52) U.S. Cl.
CPC ........... *A61B 5/4839* (2013.01); *A61B 5/14532* (2013.01); *G06F 19/3456* (2013.01)
USPC ........... 600/365; 600/300; 600/319; 600/347; 600/316

(58) Field of Classification Search
CPC ................. A61B 5/14532; A61B 5/14865
USPC ............... 600/365, 316, 345, 347, 319, 300; 514/5.9, 6.1, 6.2, 6.3, 6.7, 6.8
See application file for complete search history.

(56) References Cited

U.S. PATENT DOCUMENTS

| | | | |
|---|---|---|---|
| 4,731,726 | A | 3/1988 | Allen |
| 5,251,126 | A | 10/1993 | Kahn et al. |
| 5,822,715 | A | 10/1998 | Worthington et al. |
| 6,179,979 | B1 | 1/2001 | Hodges et al. |
| 6,193,873 | B1 | 2/2001 | Ohara et al. |
| 6,280,409 | B1 | 8/2001 | Stone et al. |
| 6,284,125 | B1 | 9/2001 | Hodges et al. |

(Continued)

FOREIGN PATENT DOCUMENTS

| | | |
|---|---|---|
| CN | 1461215 A | 12/2003 |
| CN | 101238466 A | 8/2008 |

(Continued)

OTHER PUBLICATIONS

International PCT Patent Application No. PCT/US2010/040434, International Search Report, dated Oct. 20, 2010, 3 pgs, European Patent Office, Rijswijk.

(Continued)

*Primary Examiner* — Patricia Mallari
*Assistant Examiner* — Tho Tran

(57) ABSTRACT

Various embodiments are described and illustrated to calculate an insulin bolus, recommend such bolus, and provide reminder messages for performing an additional glucose test.

4 Claims, 17 Drawing Sheets

(56) References Cited

U.S. PATENT DOCUMENTS

| | | |
|---|---|---|
| 6,309,884 B1 | 10/2001 | Cooper et al. |
| 6,379,301 B1 | 4/2002 | Worthington et al. |
| 6,413,410 B1 | 7/2002 | Hodges et al. |
| 6,425,863 B1 | 7/2002 | Werner et al. |
| 6,475,372 B1 | 11/2002 | Ohara et al. |
| 6,544,212 B2 | 4/2003 | Galley et al. |
| 6,558,351 B1 | 5/2003 | Steil et al. |
| 6,572,542 B1 | 6/2003 | Houben et al. |
| 6,633,772 B2 | 10/2003 | Ford et al. |
| 6,635,167 B1 | 10/2003 | Richards et al. |
| 6,656,114 B1 | 12/2003 | Poulsen et al. |
| 6,691,043 B2 | 2/2004 | Ribeiro, Jr. |
| 6,716,577 B1 | 4/2004 | Yu et al. |
| 6,749,887 B1 | 6/2004 | Dick et al. |
| 6,862,466 B2 | 3/2005 | Ackerman |
| 6,863,801 B2 | 3/2005 | Hodges et al. |
| 6,890,421 B2 | 5/2005 | Ohara et al. |
| 6,941,163 B2 | 9/2005 | Ford et al. |
| 7,022,072 B2 | 4/2006 | Fox et al. |
| 7,024,236 B2 | 4/2006 | Ford et al. |
| 7,045,046 B2 | 5/2006 | Chambers et al. |
| 7,060,059 B2 | 6/2006 | Keith et al. |
| 7,179,226 B2 | 2/2007 | Crothall et al. |
| 7,204,823 B2 | 4/2007 | Estes et al. |
| 7,241,265 B2 | 7/2007 | Cummings et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,291,256 B2 | 11/2007 | Teodorczyk et al. |
| 7,354,420 B2 | 4/2008 | Steil et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,498,132 B2 | 3/2009 | Yu et al. |
| 7,509,156 B2 | 3/2009 | Flanders |
| 7,553,281 B2 | 6/2009 | Hellwig et al. |
| 7,651,489 B2 | 1/2010 | Estes et al. |
| 2002/0019707 A1 | 2/2002 | Cohen et al. |
| 2002/0026111 A1 | 2/2002 | Ackerman |
| 2003/0108976 A1 | 6/2003 | Braig et al. |
| 2003/0125612 A1 | 7/2003 | Fox et al. |
| 2003/0175806 A1 | 9/2003 | Rule et al. |
| 2003/0208113 A1 | 11/2003 | Mault et al. |
| 2003/0211617 A1 | 11/2003 | Jones |
| 2003/0220814 A1 | 11/2003 | Gordon |
| 2004/0044272 A1* | 3/2004 | Moerman et al. ............ 600/300 |
| 2004/0059201 A1 | 3/2004 | Ginsberg |
| 2004/0180810 A1* | 9/2004 | Pilarski .......................... 514/3 |
| 2005/0004439 A1 | 1/2005 | Shin et al. |
| 2005/0027182 A1 | 2/2005 | Siddiqui et al. |
| 2005/0090726 A1 | 4/2005 | Ackerman |
| 2005/0096511 A1 | 5/2005 | Fox et al. |
| 2005/0096512 A1 | 5/2005 | Fox et al. |
| 2005/0113653 A1 | 5/2005 | Fox et al. |
| 2005/0143864 A1 | 6/2005 | Blomquist |
| 2005/0176153 A1 | 8/2005 | O'hara et al. |
| 2005/0182358 A1 | 8/2005 | Veit et al. |
| 2005/0214892 A1 | 9/2005 | Kovatchev et al. |
| 2007/0010950 A1 | 1/2007 | Abensour et al. |
| 2007/0016127 A1 | 1/2007 | Staib et al. |
| 2007/0016449 A1 | 1/2007 | Cohen et al. |
| 2007/0060803 A1 | 3/2007 | Liljeryd et al. |
| 2007/0060813 A1 | 3/2007 | Chang |
| 2007/0083335 A1 | 4/2007 | Moerman et al. |
| 2007/0118589 A1 | 5/2007 | Brown |
| 2007/0173761 A1 | 7/2007 | Kanderian et al. |
| 2007/0208246 A1 | 9/2007 | Brauker et al. |
| 2007/0231914 A1 | 10/2007 | Deng et al. |
| 2007/0232880 A1 | 10/2007 | Siddiqui et al. |
| 2007/0287985 A1 | 12/2007 | Estes et al. |
| 2008/0045819 A1 | 2/2008 | Emoto et al. |
| 2008/0045825 A1 | 2/2008 | Melker et al. |
| 2008/0052057 A1 | 2/2008 | Brown |
| 2008/0097289 A1 | 4/2008 | Steil et al. |
| 2008/0119702 A1 | 5/2008 | Reggiardo et al. |
| 2008/0119710 A1 | 5/2008 | Reggiardo et al. |
| 2008/0125636 A1 | 5/2008 | Ward et al. |
| 2008/0139910 A1 | 6/2008 | Mastrototaro et al. |
| 2008/0154513 A1 | 6/2008 | Kovatchev et al. |
| 2008/0171967 A1 | 7/2008 | Blomquist et al. |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172031 A1 | 7/2008 | Blomquist |
| 2008/0177154 A1 | 7/2008 | Hansen et al. |
| 2008/0183060 A1 | 7/2008 | Steil et al. |
| 2008/0187943 A1 | 8/2008 | Buse et al. |
| 2008/0188796 A1 | 8/2008 | Steil et al. |
| 2008/0199465 A1 | 8/2008 | Lake et al. |
| 2008/0206799 A1 | 8/2008 | Blomquist |
| 2008/0234992 A1 | 9/2008 | Ray et al. |
| 2008/0235053 A1 | 9/2008 | Ray et al. |
| 2008/0255438 A1 | 10/2008 | Saidara et al. |
| 2008/0255707 A1* | 10/2008 | Hebblewhite et al. ......... 700/283 |
| 2008/0262088 A1 | 10/2008 | Hauck et al. |
| 2008/0268485 A1 | 10/2008 | Guarino et al. |
| 2008/0269585 A1 | 10/2008 | Ginsberg |
| 2008/0294024 A1 | 11/2008 | Cosentino et al. |
| 2008/0312512 A1 | 12/2008 | Brukalo et al. |
| 2008/0312518 A1 | 12/2008 | Jina et al. |
| 2009/0006129 A1 | 1/2009 | Thukral et al. |
| 2009/0018495 A1 | 1/2009 | Panduro |
| 2009/0018779 A1 | 1/2009 | Cohen et al. |
| 2009/0030733 A1 | 1/2009 | Cohen et al. |
| 2009/0098587 A1 | 4/2009 | Hetzel et al. |
| 2009/0099506 A1 | 4/2009 | Estes et al. |
| 2009/0099509 A1 | 4/2009 | Estes et al. |
| 2009/0105570 A1 | 4/2009 | Sloan et al. |
| 2009/0112069 A1 | 4/2009 | Kanamori et al. |
| 2009/0112626 A1 | 4/2009 | Talbot et al. |
| 2009/0137455 A1 | 5/2009 | Steiner et al. |
| 2009/0149717 A1 | 6/2009 | Brauer et al. |
| 2009/0150186 A1 | 6/2009 | Cohen et al. |
| 2009/0156923 A1 | 6/2009 | Power et al. |
| 2009/0156924 A1 | 6/2009 | Shariati et al. |
| 2009/0177147 A1 | 7/2009 | Blomquist et al. |
| 2009/0184004 A1 | 7/2009 | Chatiler et al. |
| 2009/0237262 A1 | 9/2009 | Smith et al. |
| 2009/0240127 A1 | 9/2009 | Ray |
| 2009/0247982 A1 | 10/2009 | Krulevitch et al. |
| 2009/0292190 A1 | 11/2009 | Miyashita |
| 2010/0016700 A1 | 1/2010 | Sieh et al. |
| 2010/0041084 A1 | 2/2010 | Stephens et al. |
| 2010/0041960 A1 | 2/2010 | Yuan |
| 2010/0174228 A1 | 7/2010 | Buckingham et al. |

FOREIGN PATENT DOCUMENTS

| | | |
|---|---|---|
| CN | 101288593 A | 10/2008 |
| EP | 0483595 | 12/2001 |
| EP | 1338295 A1 | 8/2003 |
| EP | 1568310 A1 | 8/2005 |
| EP | 1677226 | 7/2006 |
| EP | 1770396 A2 | 4/2007 |
| EP | 1840219 A1 | 10/2007 |
| JP | 2002336206 A | 11/2002 |
| JP | 2004519031 A | 6/2004 |
| JP | 2008229331 A | 10/2008 |
| JP | 2009502443 A | 1/2009 |
| JP | 2010502361 A | 1/2010 |
| WO | WO 98/37805 A1 | 9/1998 |
| WO | WO 02/00112 A2 | 1/2002 |
| WO | WO 03/030731 A2 | 4/2003 |
| WO | WO 03/045233 A1 | 6/2003 |
| WO | WO 2004/015539 A2 | 2/2004 |
| WO | WO 2004/023972 A2 | 3/2004 |
| WO | WO 2005/093629 A2 | 10/2005 |
| WO | WO 2006/066038 A3 | 6/2006 |
| WO | WO 2006/066583 A1 | 6/2006 |
| WO | WO 2006/133348 A2 | 12/2006 |
| WO | WO 2007/005170 A2 | 1/2007 |
| WO | WO 2007/019289 A1 | 2/2007 |
| WO | WO 2007/019384 A1 | 2/2007 |
| WO | WO 2007/028271 A3 | 3/2007 |

(56) References Cited

FOREIGN PATENT DOCUMENTS

| WO | WO 2007/101260 A2 | 9/2007 |
|---|---|---|
| WO | WO 2007/149533 A1 | 12/2007 |
| WO | 2008030347 A2 | 3/2008 |
| WO | WO 2008/071218 A1 | 6/2008 |
| WO | WO 2008/071444 A1 | 6/2008 |
| WO | WO 2008/073609 A2 | 6/2008 |
| WO | WO 2008/094249 A1 | 8/2008 |
| WO | WO 2009/005952 A3 | 1/2009 |
| WO | WO 2009/005960 A3 | 1/2009 |
| WO | WO 2009/016050 A1 | 2/2009 |
| WO | WO 2009/137661 | 11/2009 |

OTHER PUBLICATIONS

International Search Report, PCT Application No. PCT/US2010/040383, dated Nov. 4, 2010, 3 pages, European Patent Office, Rijswijk.
International Search Report, PCT Application No. PCT/US2010/040425, Dated Dec. 23, 2010, 7 pages, European Patent Office, Rijswijk, Netherlands.
Partial International Search Report, Annex to Form PCT/ISA/206, PCT Application No. PCT/US2010/040309, Dated Nov. 29, 2010, 2 pages, European Patent Office, Rijswijk, Netherlands.
International Search Report, PCT Application No. PCT/GB2010/001683, Dated Dec. 22, 2010, 4 pages, European Patent Office, Rijswijk, Netherlands.
Nathan, D.M., *Management of Hyperglycemia in Type 2 Diabetes: A Consensus Algorithm for the Initiation and Adjustment of Therapy*, Diabetes Care, vol. 29 No. 8, 1963-1972, Aug. 2006.
William H. et al. *Numerical Recipes in C: The Art of Scientific Computing*. Cambridge: Cambridge University Press, 1992. ISBN 0-521-43108-5, pp. 226-230.
"Accu-Chek Complete Owner's Booklet", Roche Diagnostics, 2004, XP002636883, Retrieved from internet: URL:https://www.accu-chek.com/us/customer-care/downloads.html [retrieved May 12, 2011], p. 8, pp. 33-40, pp. 46 and 86.
International Search Report, PCT Application No. PCT/US2010/040443, dated May 17, 2011, 3 pages, European Patent Office, Rijswijk, NL.
First Office Action issued in related Chinese Patent Application No. 201080055124.X, dated Nov. 27, 2013, 15 pages.
Second Office Action issued in related Chinese Patent Application No. 201080055124.X, dated Jul. 10, 2014, 32 pages.
First Search Report issued in related Chinese Patent Application No. 201080055124.X, dated Nov. 19, 2013, 3 pages.
Supplementary Search Report issued in related Chinese Patent Application No. 201080055124.X, dated Jun. 27, 2014, 3 pages.
European Search Report issued in related European Patent Application No. 10733069.8, dated Aug. 6, 2013, 4 pages.
European Search Report issued in related European Patent Application No. 13174423.7, dated Aug. 6, 2013, 10 pages.
European Search Report issued in related European Patent Application No. 13192487.0, dated Dec. 16, 2013, 8 pages.
Notification of Reason for Refusal issued in related Japanese Patent Application No. 2012-532072, dated Apr. 8, 2014, 5 pages.
Written Opinion issued in related International Application No. PCT/US2010/040425, dated Dec. 23, 2010, 13 pages.
Official Action issued in related Russian Application No. 2012117828, dated Jun. 10, 2014, 15 pages.

\* cited by examiner

ANALYTE TESTING METHOD AND DEVICE FOR DIABETES MANAGEMENT

This application claims the benefits of priority under 35 USC§119 and/or §120 from prior filed U.S. Provisional Application Ser. No. 61/246,630 filed on Sep. 29, 2009, which application is incorporated by reference in their entirety into this application.

BACKGROUND

Introduction and management of insulin therapy to a patient with diabetes may be overwhelming to the patient and a burden to the provider due to the complexity of conventional methods and devices for doing so. Significant training of the patient may be necessary. The patient may need to learn, for example, various concepts and actions including hypoglycemia management, injections and the proper use of insulin administration devices, as well as the mechanical, electronic, and software aspects of using a blood glucose meter. In addition, the patient must learn to follow the doctor's instructions in starting and adjusting insulin dosages on a regular basis (e.g., per meal, daily, 2× weekly, or weekly basis).

Detailed instructions as to the prescribed blood glucose testing and insulin titration protocol are typically written out by the health care professional and checked off on a piece of paper. Patients often keep handwritten logs in order to comply.

It is not uncommon for a patient to have poor glycemic control even after getting onto insulin therapy. The care provider (i.e., physician) is then confronted with a challenging situation in trying to determine if the poor glycemic control is due to an inadequate frequency of glucose testing, incorrect processing of data for determining an insulin bolus amount, or a combination thereof.

SUMMARY OF THE DISCLOSURE

Applicants have developed certain improvements to alleviate some of the shortcomings discussed above. Specifically, applicants have recognized that in order to deliver effective therapy to a diabetes subject, the therapy should be implemented into the health monitoring device. Hence, in one embodiment, a method of managing blood glucose value of a diabetes user is provided. The method may be achieved by: conducting a plurality of glucose measurements from physiological fluids of a user with a glucose measurement unit coupled to a data management unit; verifying whether a most recent glucose measurement was made within a first predetermined time period; based on the user's selection, recommending an insulin bolus amount for (a) glucose correction only; (b) carbohydrate coverage only; or (c) both carbohydrate and glucose correction; and annunciating the insulin bolus recommendation. The first predetermined time period may range from about 15 minutes to about 120 minutes, preferably range from about 60 to about 120 minutes, and more preferably range from about 90 minutes to about 120 minutes.

In another embodiment, a method of managing blood glucose value of a diabetes user is provided. The method may be achieved by: conducting a plurality of glucose measurements from physiological fluids of a user with a glucose measurement unit coupled to a data management unit; verifying whether a most recent glucose measurement was made within a first predetermined time period; querying the user as to whether an insulin calculation was utilized by the user in the last predetermined amount of time and if true, warning the user that insulin may still be physiologically active to the user in a situation during which the user took insulin and recommending an insulin bolus based on both carbohydrate coverage and glucose correction. The predetermined amount of time may range from about 3 hours to about 5 hours.

In a further embodiment, a method of managing blood glucose value of a diabetes user is provided. The method may be achieved by: conducting a plurality of glucose measurements from physiological fluids of a user with a glucose measurement unit coupled to a data management unit; verifying whether a most recent glucose measurement was made within a first predetermined time period; determining an insulin bolus for delivery to the user based on at least one of the plurality of blood glucose measurement values, insulin sensitivity of the user, insulin to carbohydrate ratio, and target glucose value; and reminding the user to conduct a glucose measurement within a second predetermined time period whenever a glucose measurement from the user's physiological fluid indicates an abnormal glucose value.

In yet another embodiment, a method of managing blood glucose value of a diabetes user is provided. The method may be achieved by: flagging a glucose measurement conducted by the user as a fasting glucose measurement; in the event the flagged fasting glucose measurement is less than a first threshold, reminding the user to conduct another glucose measurement after a first retest time period; in the event the flagged fasting glucose measurement is greater than a second threshold, reminding the user to conduct another glucose measurement after a second retest time period.

In a further embodiment, method of notifying a diabetes user of certain glycemic condition of the user with an analyte measurement and management device is provided. The method may be achieved by: conducting a glucose measurement before a meal with the analyte measurement and management device; flagging the before meal glucose measurement in a memory of the test meter as a pre-meal glucose value;

conducting a glucose measurement after a meal with the analyte measurement and management device; flagging the after-meal glucose measurement in the memory of the test meter as a post-meal value; determining whether a difference between the flagged post-meal glucose value and flagged pre-meal glucose value is within about 50 mg/dL (or its conversion into milliMole per Liter unit); and notifying the user whenever the difference is greater than about 50 mg/dL (or its conversion into mmol/L unit or milliMole per Liter) and reminding the user to re-test in a second retest time period.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Embodiments described and illustrated herein provide an analyte (e.g., blood glucose) measurement and management device and associated methods that simplify training and guide a patient regarding when to measure an analyte (i.e., to "test") and how much and when to administer a therapeutic agent (such as insulin) in a simple and convenient manner and with a minimum of devices. Embodiments of the analyte measurement and management device and system are also beneficial to care providers (for example, physicians) by gathering, organizing and storing information that provides insight into how effective a patient is in following a prescribed analyte management regimen.

Figure 1:
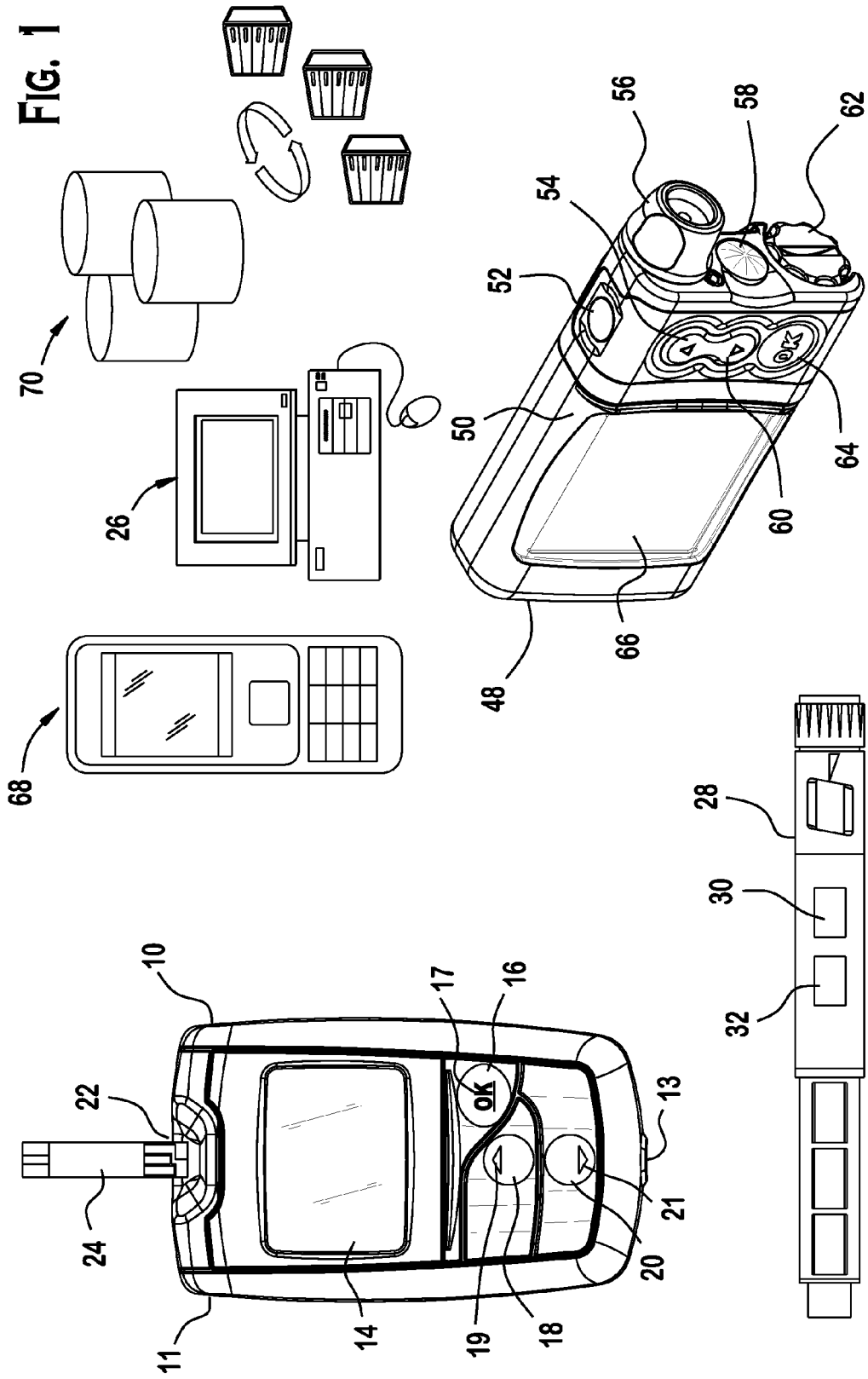
FIG. 1 illustrates a diabetes management system that includes an analyte measurement and management device, therapeutic dosing devices, and data communication devices, according to an exemplary embodiment described and illustrated herein.

FIG. 1 illustrates a diabetes management system that includes an analyte measurement and management device 10, therapeutic dosing devices (28 and 48), and data communication devices (68, 26, and 70). Analyte measurement and management device 10 may be configured to wirelessly communicate with a data management unit or DMU such as, for example, an insulin pen 28, an insulin pump 48, a mobile phone 68, a personal computer 26 (including a mobile computer), or a network server 70, or through a combination of the exemplary data management unit devices described herein. As used herein, the nomenclature "DMU" represents either individual unit 28, 48, 68, 26 or 70 separately or all of the data management units (28, 48, 68, 26, and 70) usable together in a disease management system. Note that analyte measurement and management device 10 may be referred to as a glucose meter, a meter, an analyte measurement device, and a testing device.

Figure 2:
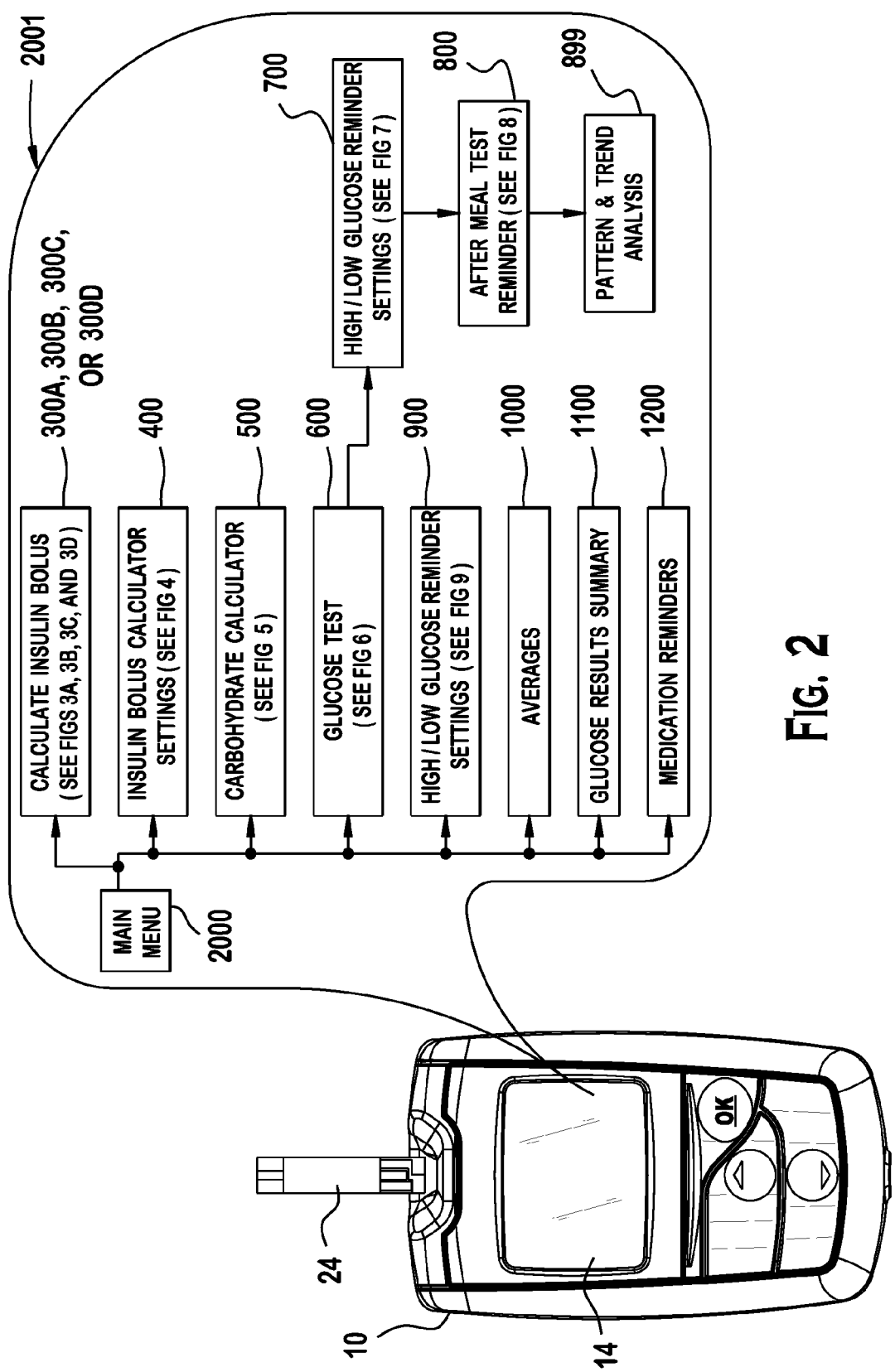
FIG. 2 illustrates a user interface of the analyte measurement and management device for managing diabetes, according to an exemplary embodiment described and illustrated herein.

FIG. 2 illustrates a user interface 2001 implemented in, for example, the meter 10. In the exemplary implementation, the user interface 2001 provides recommendations and warnings to a user as part of the user's diabetes management. In such embodiment, programs and methods for conducting user interface 2001 may be stored on a non-volatile memory portion of glucose meter 10. Steps and instructions of user interface 2001 may be communicated on a communication output unit such as, for example, a display 14 of glucose meter 10. In such embodiment, the diabetes management 2001 may be implemented using meter 10 without the need for an external computer, personal digital assistant, or wireless insulin pump. As used herein, the term "user" is intended to indicate primarily a mammalian subject (e.g., a person) who has diabetes but which term may also include a caretaker or a healthcare provider who is operating the meter 10 on behalf of the diabetes subject.

Figure 11:
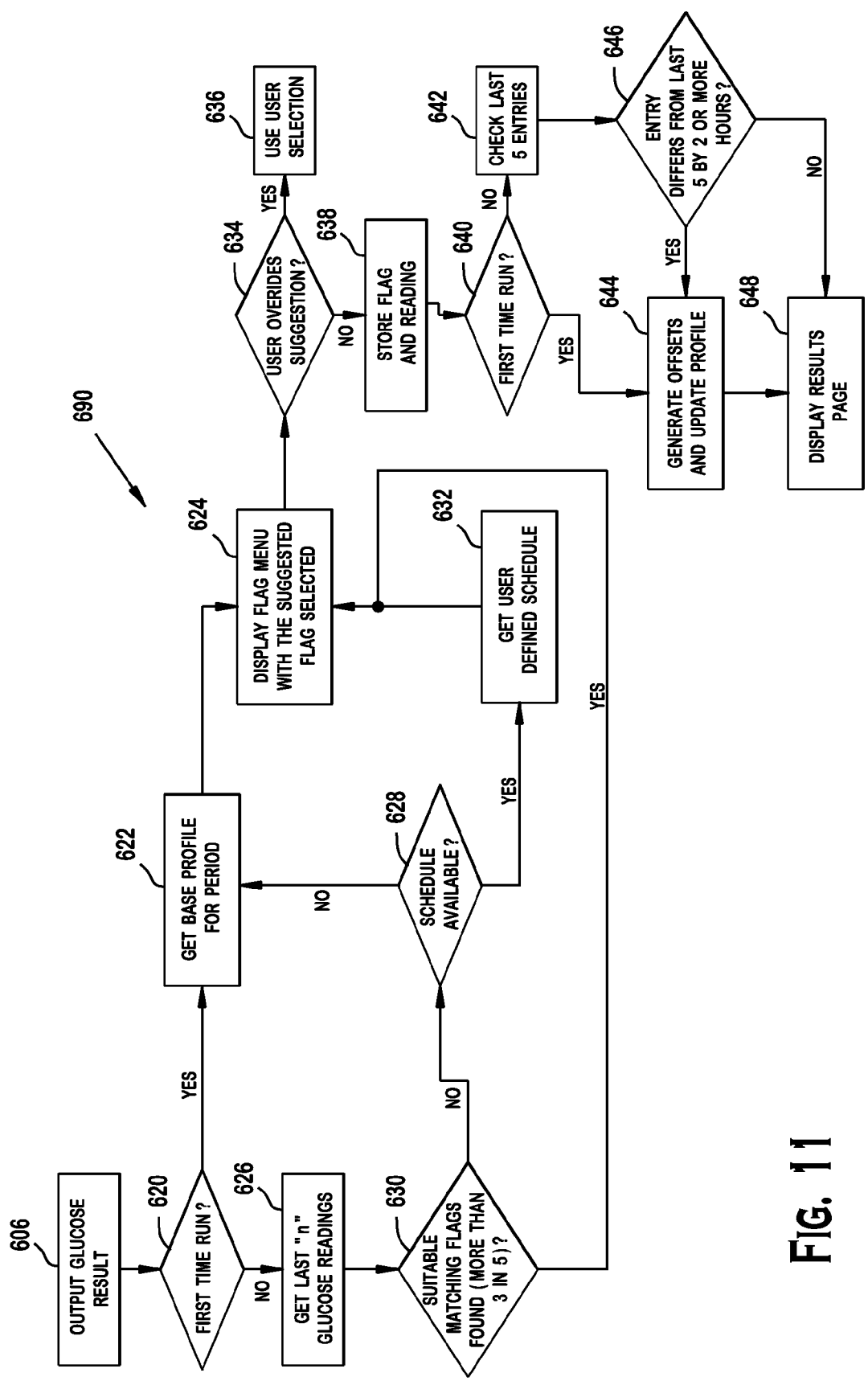
FIG. 11 is a flow chart illustrating an embodiment of a method for predicting a type of flag to recommend to a user for inputting into the diabetes management system.

A user may select a particular function or sub-routine from a list of selections within a main menu 2000. The list may include the following functions that are to calculate an insulin bolus 300, configure settings for insulin bolus calculator 400, calculate a carbohydrate amount 500, perform a glucose test 600, configure settings for a high/low glucose reminder 900, communicate glucose value or concentration averages 1000, communicate glucose value or concentration summary 1100, and perform medication reminders 1200. When performing glucose test 600, the following sub-routines may also be performed which include a high/low glucose reminder 700, after meal test reminder 800, and a pattern and trend analysis 899. Alternatively, glucose test 600 may be appended to have a method 690 for predicting a type of flag to recommend to a user for inputting into the diabetes management system (FIG. 11).

A user or the HCP may select a method for calculating an insulin bolus 300 from the main menu. Note that insulin bolus calculation 300 may be one of several embodiments such as 300A, 300B, 300C, and 300D or a combination of all of these embodiments together. Briefly, three types of insulin boluses are described herein, which are an insulin bolus amount for: (a) carbohydrate coverage, (b) glucose correction, or (c) a combination thereof. The insulin bolus amount for carbohydrate coverage may be an amount of insulin needed to account for carbohydrates about to be consumed at a meal. The insulin bolus amount for a glucose measurement correction may be an amount of insulin needed to account for a user's measured glucose value that is greater than the euglycemic zone. The combination (e.g., carbohydrate value and measured glucose value) correction may be an amount of insulin needed to account for carbohydrates about to be consumed and the user's measured glucose value.

Figure 3A:
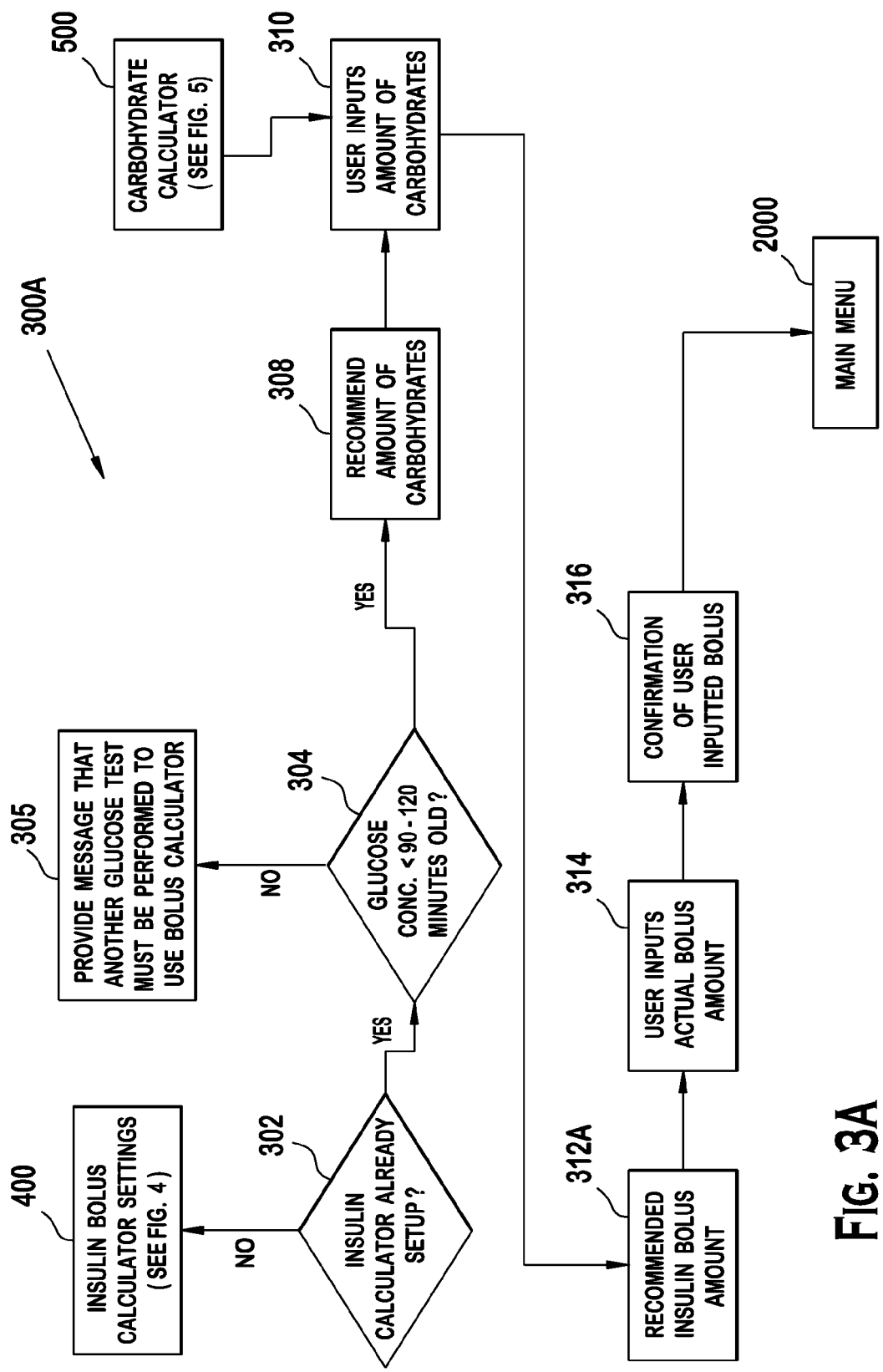
FIG. 3A is a flow chart illustrating an embodiment of a method for calculating an insulin bolus, according to an exemplary embodiment described and illustrated herein.

FIG. 3A is a flow chart illustrating an embodiment of a method for calculating an insulin bolus 300A with a carbohydrate and glucose corrections. Initially, the meter may determine whether the insulin calculator is already setup, as shown in a step 302. If the insulin calculator is not setup, then the method may move to an insulin bolus calculator settings function 400 (described below). If the insulin calculator has been setup, then the interface 2001 (which is implemented exemplarily in meter 10) may determine whether the last glucose value or concentration of the user measured is less than about 90 minutes to about 120 minutes old, as shown in a step 304. A message may be annunciated that another glucose test must be performed to use the bolus calculator, as shown in a step 305, when the last glucose value or concentration of the user measured is not less than about 90 minutes to about 120 minutes old. As used here, the term "annunciated" and variations on the root term indicate that an announcement may be provided via text, audio, visual or a combination of all modes of communication to a user, a caretaker of the user, or a healthcare provider.

A recommended amount of carbohydrates may be outputted, as shown in a step 308, where the glucose value or concentration of the user is less than about 90 minutes to about 120 minutes old. The user has the option to input the recommended amount of carbohydrates or a different value, as shown in a step 310. The amount of carbohydrate may represent an amount that is about to be consumed by the user. As a non-limiting example, the amount of carbohydrates inputted may range from about zero to about 999 grams. In another scenario, a carbohydrate calculator 500 (described below) may be used to determine the amount of carbohydrates that is inputted at step 310.

After inputting the amount of carbohydrates, a recommended insulin bolus may be outputted, as shown in a step 312A. Note that the recommended insulin bolus amount includes both an insulin bolus amount for carbohydrate coverage and an insulin correction of a recent measured glucose value of the user. The user has the option to input the recommended amount of insulin or a different value, as shown in a step 314, such as, for example, about zero to about 999 units. A confirmation of the inputted bolus amount may be annunciated to the user, as shown in a step 316, which is then followed by returning to main menu 2000.

Figure 3B:
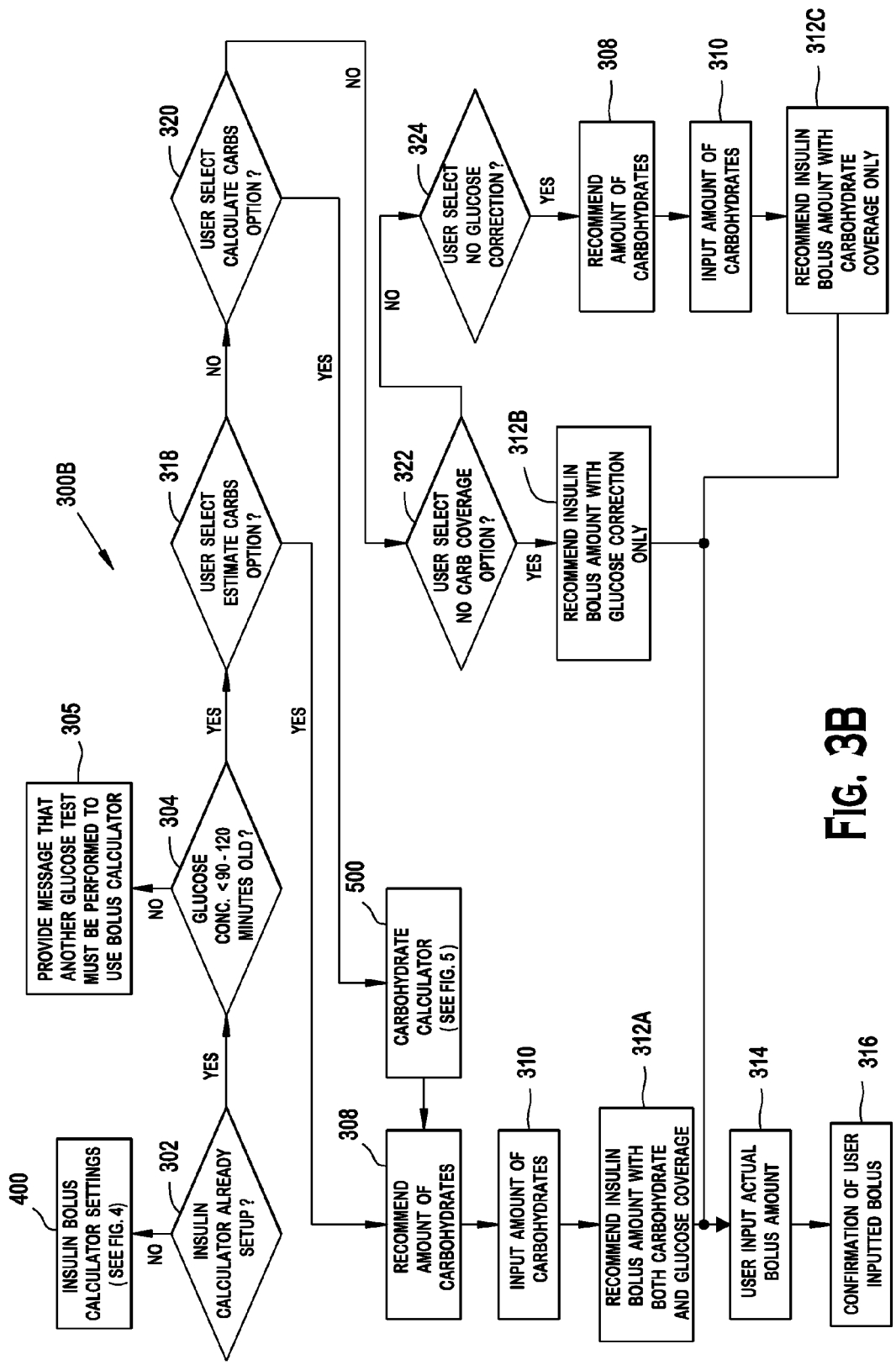
FIG. 3B is a flow chart illustrating another embodiment of a method for calculating an insulin bolus with either a glucose correction only, a carbohydrate coverage only, or a combination of a glucose and carbohydrate coverage together, according to an exemplary embodiment described and illustrated herein.

FIG. 3B is a flow chart illustrating another embodiment of a method for calculating an insulin bolus 300B. In contrast to the method 300A, the method 300B allows the user to calculate an insulin bolus that has an insulin bolus amount for carbohydrate coverage, a glucose correction, or a combination thereof. Once it has been determined that the glucose value or concentration of the user was performed in less than a first predetermined time period (e.g., from about 90 minutes to about 120 minutes old), as shown in step 304, the user is given the option to estimate carbohydrates for the insulin bolus amount for carbohydrate coverage, as shown in a step 318. The user may be given the option to select an estimate carbohydrate option (a step 318), a calculate carbohydrate option (a step 320), a no carbohydrate option (a step 322), or a no glucose correction (a step 324). As used herein the term "measured glucose value" is used to denote a glucose amount present in a physiological sample of the user or an approximate concentration in the user. The term "measured glucose value" is also used interchangeably with the term "measured glucose concentration" herein.

A recommended amount of carbohydrates that is about to be consumed may be outputted if the user selects the estimate carbohydrates option, as shown in a step 308. The estimate carbohydrate option causes a bolus amount to be determined that includes both a carbohydrate and glucose correction. As a default, the recommended amount of carbohydrates may range from about 30 grams to about 50 grams, and preferably be about 30 grams. A 30 gram default value is believed to be a relatively low value and reduces the risk that a user will overdose an insulin bolus. In another embodiment, the recommended amount of carbohydrate may be the last value inputted by the user. The user has the option to input the recommended amount of carbohydrates or a different value, as shown in a step 310. After inputting the amount of carbohydrates, a recommended insulin bolus is outputted that includes both an insulin bolus amount for carbohydrate coverage and an insulin correction, as shown in step 312A. The user has the option to input the recommended amount of insulin or a different value, as shown in a step 314. A confirmation of the inputted bolus amount may be annunciated to the user, as shown in a step 316.

The user may select the calculate carbohydrate option, as shown in a step 320. The calculate carbohydrate option provides a software database tool for determining an amount of carbohydrates using the carbohydrate calculator 500 (described below). The output of carbohydrate calculator 500 may then be inputted into step 308. The user has the option to input the recommended amount of carbohydrates or a different value, as shown in a step 310. After inputting the amount of carbohydrates, a recommended insulin bolus is outputted that includes both an insulin bolus amount for carbohydrate coverage and an insulin correction, as shown in step 312A. The user has the option to input the recommended amount of insulin or a different value, as shown in a step 314. A confirmation of the inputted bolus amount may be annunciated to the user, as shown in a step 316.

The user may select the no insulin bolus amount for carbohydrate coverage (i.e., "no-carb correction"), as shown in a step 322, which causes the recommended insulin bolus to be outputted for glucose correction only, as shown in a step 312B. The user has the option to input the recommended amount of insulin or a different value, as shown in a step 314. A confirmation of the inputted bolus amount may be annunciated to the user, as shown in a step 316.

The user may select the no glucose correction, as shown in a step 324, which causes a recommended amount of carbohydrates to be outputted that is about to be consumed, as shown in a step 308. The user has the option to input the recommended amount of carbohydrates or a different value, as shown in a step 310. After inputting the amount of carbohydrates, a recommended insulin bolus amount may be outputted for insulin bolus amount for carbohydrate coverage only, as shown in step 312C. The user has the option to input the recommended amount of insulin or a different value, as shown in a step 314. A confirmation of the inputted bolus amount may be annunciated to the user, as shown in a step 316. The method 300B allows a user to customize the insulin bolus to account for carbohydrates that are about to be consumed, a current measured glucose value, or a combination thereof.

Figure 3C:
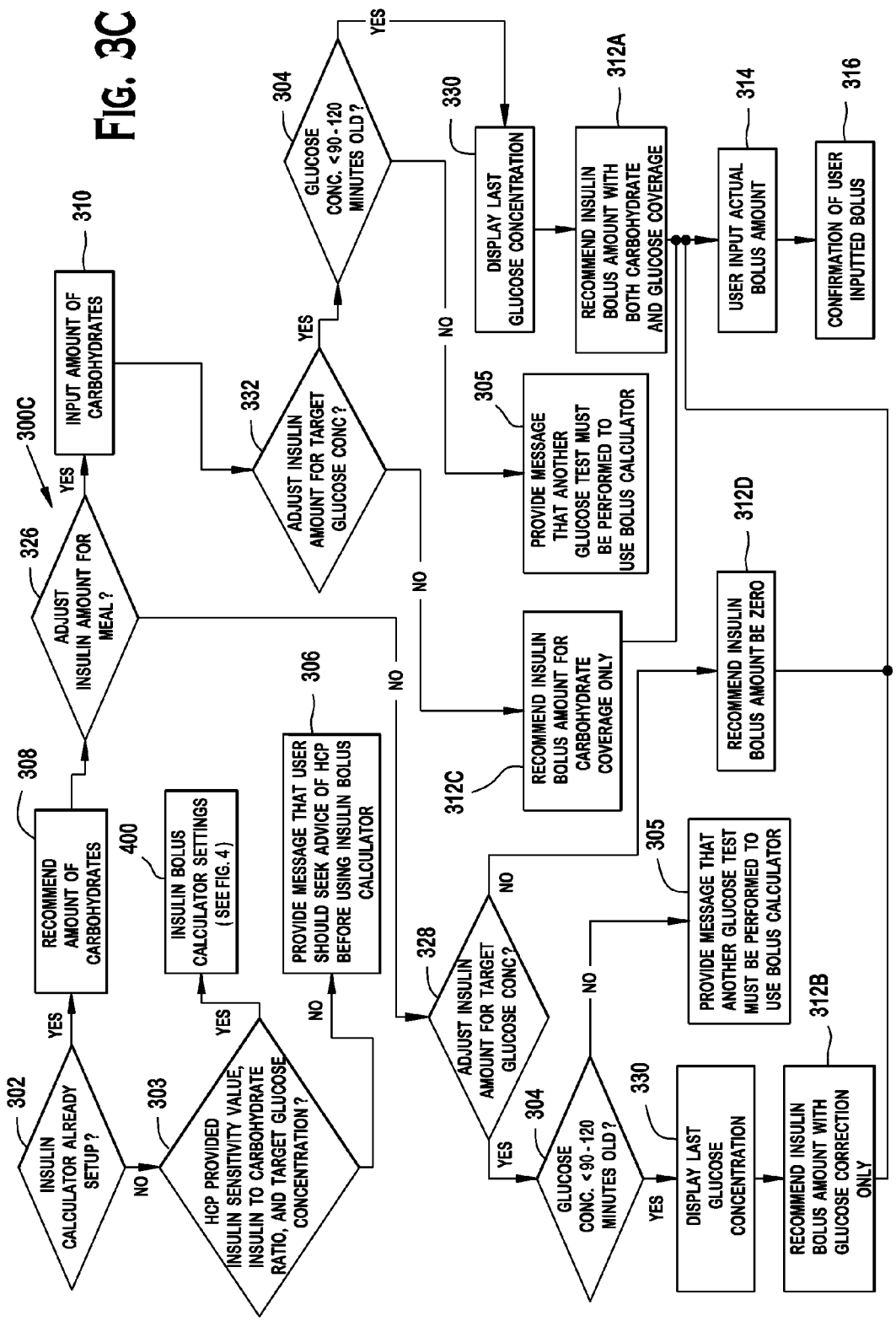
FIG. 3C is a flow chart illustrating yet another embodiment of a method for calculating an insulin bolus with either a glucose correction only, a carbohydrate coverage only, or both glucose and carbohydrate coverage together, according to an exemplary embodiment described and illustrated herein.

FIG. 3C is a flow chart illustrating another embodiment of a method for calculating an insulin bolus 300C. The method 300C allows the user to calculate an insulin bolus that has an insulin bolus amount for carbohydrate coverage, a glucose correction, or a combination thereof by asking the user whether to adjust insulin based on a meal and/or a target glucose value or concentration of the user. A recommended amount of carbohydrates to be consumed may be outputted to the user (step 308) after the insulin calculator has been set up (step 302). Next, the user may be given the option to adjust insulin for a meal, as shown in a step 326. If the insulin calculator has not been set up, then the meter may query whether a HCP has provided an insulin sensitivity value, insulin to carbohydrate ratio, and target glucose value or concentration of the user, as shown in a step 303. The meter may move to the insulin bolus calculator settings if the user has the relevant values, as shown in a step 400. Otherwise, the meter may provide a message that the user should seek the advice of a HCP before using the insulin bolus calculator, as shown in a step 306.

If the user elects to not adjust insulin for a meal, then the user may be given the option to adjust insulin based on a current measured glucose value or concentration, as shown in a step 328. If the user also elects to not adjust insulin based on the current measured glucose value or concentration, a recommended insulin bolus amount of zero may be outputted, as shown in a step 312D. However, if the user does opt to adjust insulin based on the current measured glucose value or concentration, then it must be determined that the most recent measured glucose value or concentration is less than about 90 minutes to about 120 minutes old, as shown in step 304. A message may be provided that another glucose test must be performed to use the bolus calculator, as shown in a step 305, when the last glucose value or concentration of the user measured is not less than about 90 minutes to about 120 minutes old. Otherwise, the last measured glucose value or concentration may be communicated, as shown in a step 330. Next, a recommended insulin bolus for glucose correction only may be outputted, as shown in a step 312B. The user has the option to input the recommended amount of insulin or a different value, as shown in a step 314. A confirmation of the inputted bolus amount may be annunciated to the user, as shown in a step 316.

If the user elects to adjust insulin for a meal, then the user may input an amount of carbohydrates, as shown in a step 310. Next, the user may be given the option to adjust insulin based on a current measured glucose value or concentration, as shown in a step 332. If the user also elects to not adjust insulin based on the current measured glucose value or concentration, a recommended insulin bolus amount may be outputted for insulin bolus amount for carbohydrate coverage only, as shown in a step 312C. However, if the user does opt to adjust insulin based on the current measured glucose value or concentration, then it must be determined that the most recent measured glucose value or concentration is less than about 90 minutes to about 120 minutes old, as shown in step 304. A message may be provided that another glucose test must be performed to use the bolus calculator, as shown in a step 305, when the last glucose value or concentration of the user measured is not less than about 90 minutes to about 120 minutes old. Otherwise, the last measured glucose value or concentration may be communicated, as shown in a step 330. Next, a recommended insulin bolus that includes both an insulin bolus amount for carbohydrate coverage and an insulin correction, as shown in step 312A. After step 312A or 312C, the user has the option to input the recommended amount of insulin or a different value, as shown in a step 314. A confirmation of the inputted bolus amount may be annunciated to the user, as shown in a step 316.

Figure 3D:
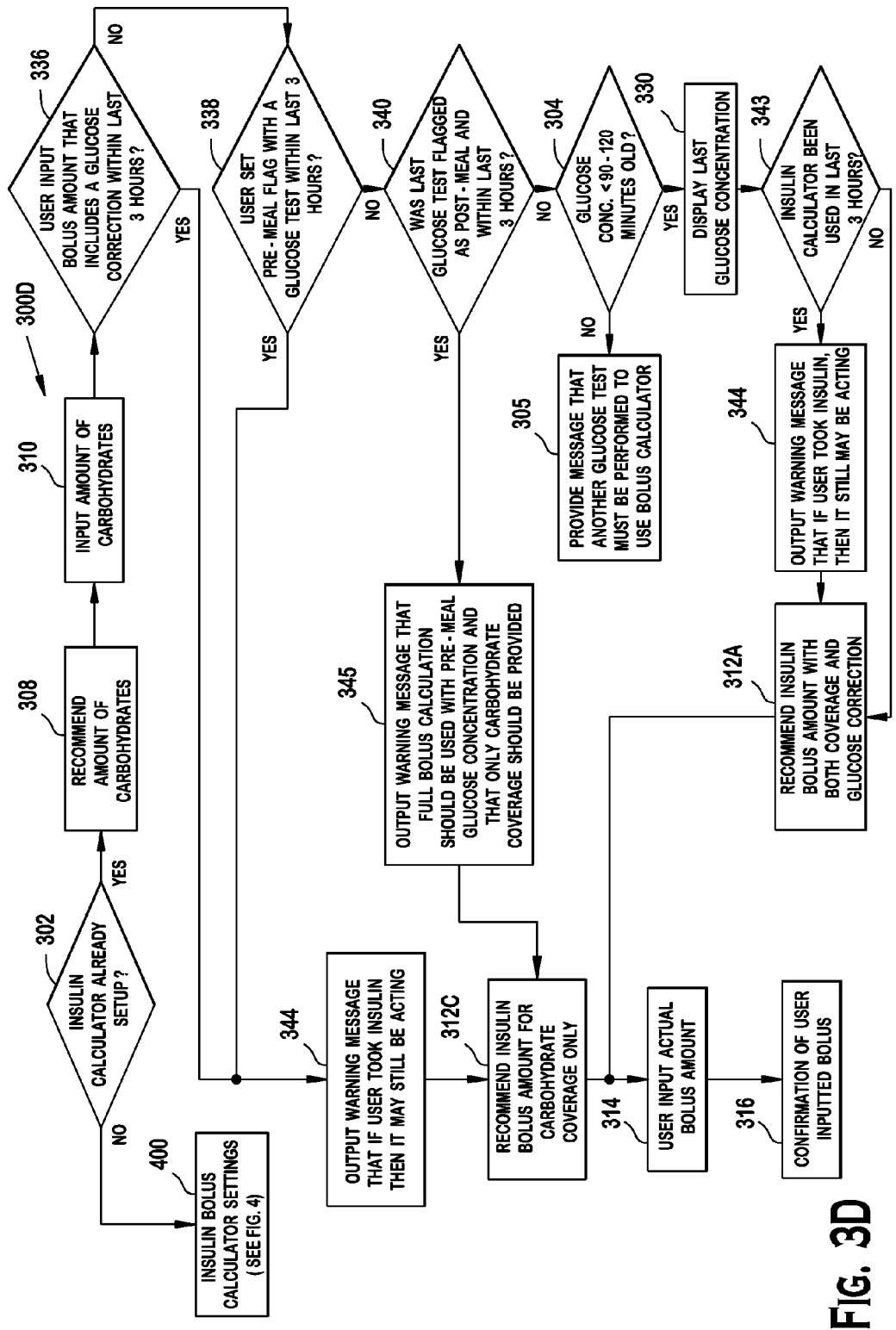
FIG. 3D is a flow chart illustrating another embodiment of a method for calculating an insulin bolus that includes a warning that insulin may still be physiologically active to the user in a situation during which the user took insulin, according to an exemplary embodiment described and illustrated herein.

FIG. 3D is a flow chart illustrating another embodiment of a method for calculating an insulin bolus 300D. The method 300D allows the user to calculate an insulin bolus that has an insulin bolus amount for carbohydrate coverage, a glucose correction, or a combination thereof and accounts for the possibility of having insulin on board. The term insulin on board refers to a situation where a previous insulin bolus inside a user's body is still affecting the metabolism of glucose. If a user has insulin on board and inputs another insulin bolus, there is a risk of hypoglycemia.

A recommended amount of carbohydrates to be consumed may be outputted to the user (step 308) after the insulin calculator has been set up (step 302). The user then has the option to input the recommended amount of carbohydrates or a different value, as shown in a step 310. Next, the meter may perform a series of queries such as determining whether a user inputted an insulin bolus that includes a glucose correction within the last 3 hours (a step 336), whether a user set a pre-meal flag with a glucose test within the last 3 hours (a step 338), and whether the last glucose test was flagged as post-meal within the last three hours (a step 340). If there is an affirmative response to steps 336 or 338, then a warning message (e.g., text, audio, visual audio or even a message to the user's mobile phone) may be outputted that insulin may still be physiologically active to the user in a situation during which the user took insulin, as shown in a step 344. If there is an affirmative response to step 340, then a warning message should be outputted that the full bolus calculator should be used with a pre-meal glucose concentration and that only carbohydrate coverage should be provided, as shown in a step 345. Next, a recommended insulin bolus amount may be outputted for insulin bolus amount for carbohydrate coverage only, as shown in a step 312C. Note that steps 336, 338, and 340 are not limited to only 3 hours and in other embodiments, the amount of time may range from about 3 to about 5 hours. The amount of time can be set by a user or HCP where such time may be based on the pharmacokinetics of the user in responding to and metabolizing insulin.

If there is not an affirmative response for each of the steps 336, 338, and 340, then the meter may determine whether the last glucose value or concentration of the user measured is less than about 90 minutes to about 120 minutes old, as shown in a step 304. A message may be provided that another glucose test must be performed to use the bolus calculator, as shown in a step 305, when the last glucose value or concentration of the user measured is not less than about 90 minutes to about 120 minutes old. Otherwise, the last measured glucose value or concentration may be communicated, as shown in a step 330. Next, the meter may perform a query of whether the insulin calculator has been used in the last three hours, as shown in a step 343. If there is an affirmative response to step 343, then a warning message may be outputted that insulin may still be physiologically active to the user in a situation during which the user took insulin, as shown in a step 344. Next, a recommended insulin bolus amount may be outputted for carbohydrate and glucose correction, as shown in a step 312A. If there is a negative response to step 343, then no warning message is provided and a recommended insulin bolus amount is outputted for carbohydrate and glucose correction, as shown in step 312A. Similar to steps 336, 338, and 340, step 343 is not limited to only 3 hours and may range from about 3 to about 5 hours.

After steps 312A or 312C, the user has the option to input the recommended amount of insulin or a different value, as shown in a step 314. A confirmation of the inputted bolus amount may be annunciated to the user, as shown in a step 316. In summary, the method 300D provides several queries to determine whether a user has insulin on board and warns the user before another insulin bolus is administered.

Figure 4:
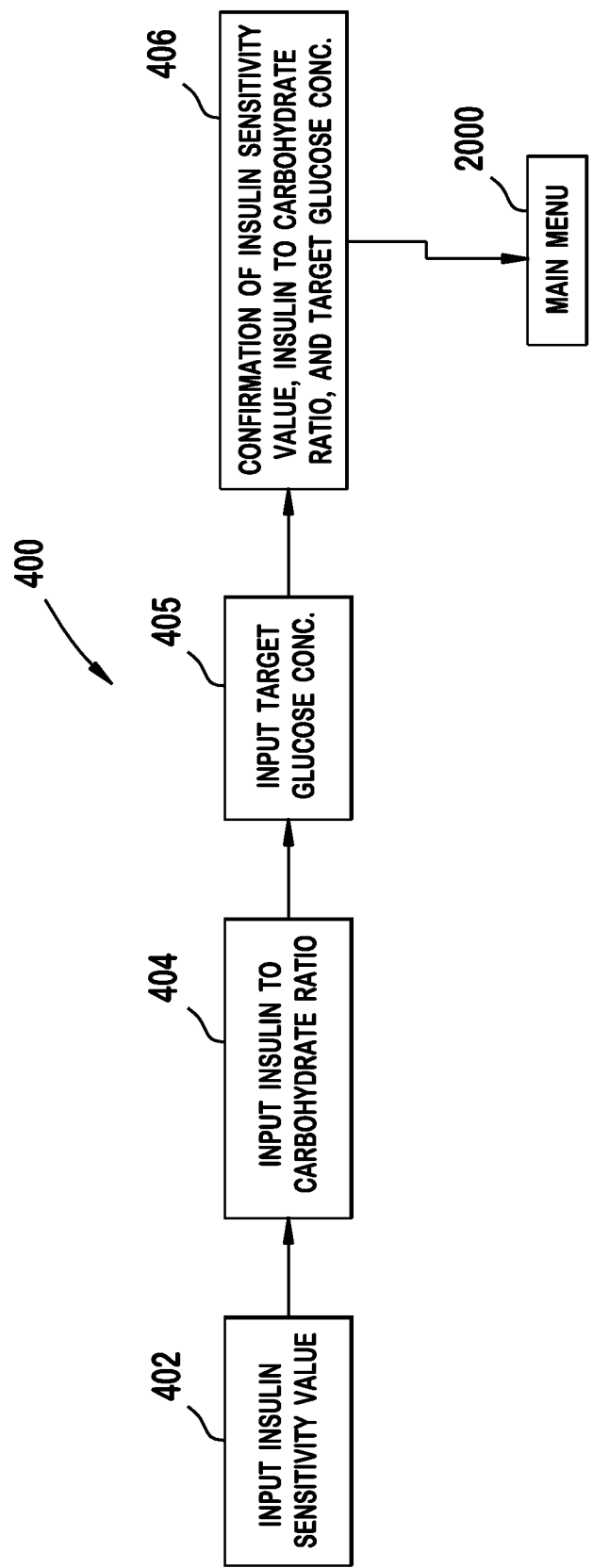
FIG. 4 is a flow chart illustrating an embodiment of a method for setting up a bolus calculator, according to an exemplary embodiment described and illustrated herein.
Figure 5:
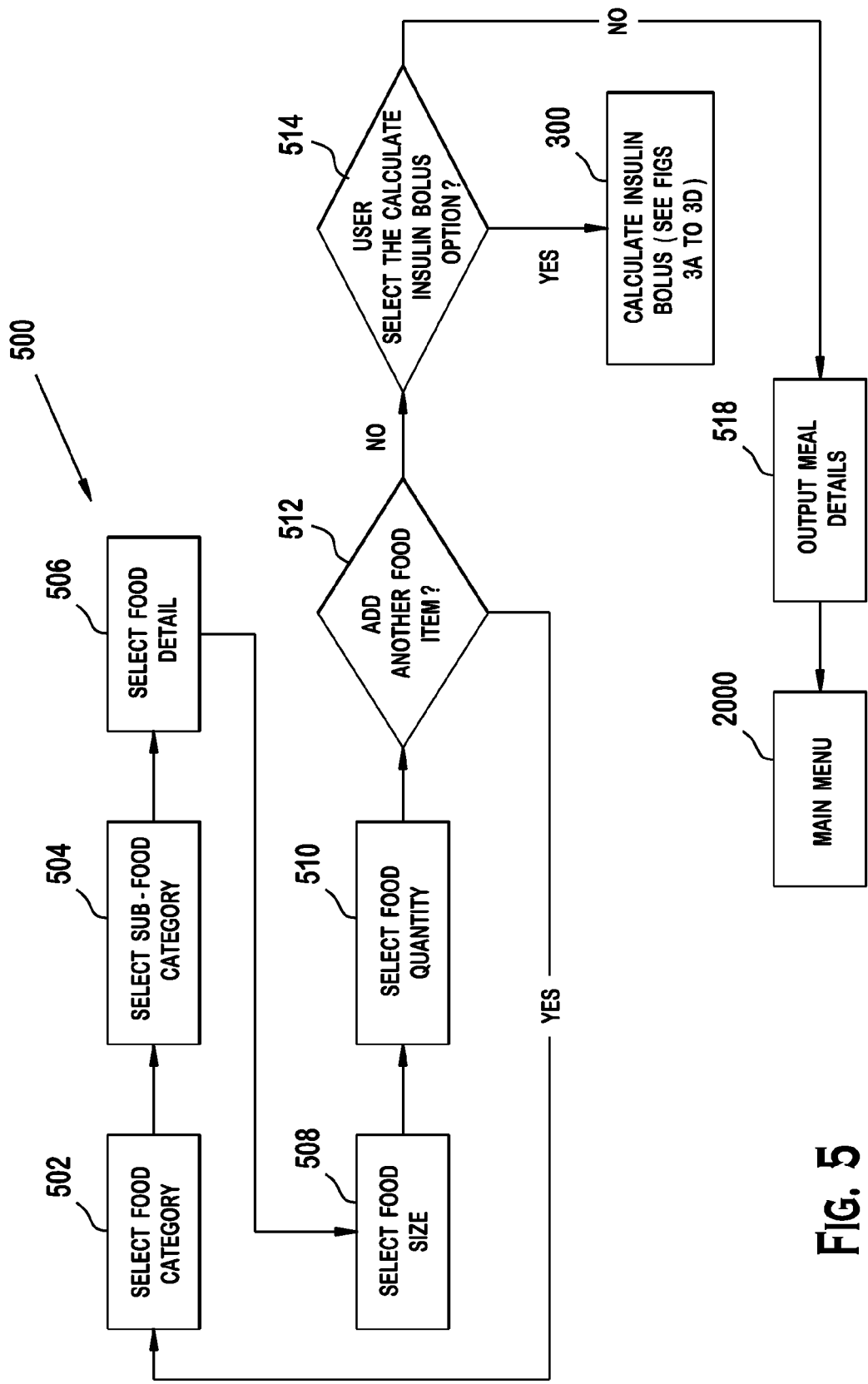
FIG. 5 is a flow chart illustrating an embodiment of a method for calculating an amount of carbohydrates, according to an exemplary embodiment described and illustrated herein.

FIG. 4 illustrates an embodiment 400 for configuring the set up of the bolus calculator 300. A user may select an insulin sensitivity value, an insulin-to-carbohydrate ratio, and a target blood glucose value, as shown in steps 402, 404, and 405. More specifically, the user may select a discrete insulin sensitivity value and an insulin-to-carbohydrate ratio for a particular meal such as breakfast, lunch, or dinner. Insulin sensitivity values may range from about 5 mg/dL (or its conversion into mmol/L unit or milliMole per Liter) to about 300 mg/dL (or its conversion into mmol/L unit or milliMole per Liter). Insulin-to-carbohydrate ratio may range from about 5 grams to about 50 grams. Target blood glucose values may range from about 60 mg/dL (or its conversion into mmol/L unit or milliMole per Liter) to about 290 mg/dL (or its conversion into mmol/L unit or milliMole per Liter). Next, a confirmation of the insulin sensitivity value and an insulin-to-carbohydrate ratio may be annunciated to the user, as shown in a step 406, which is then followed by returning to main menu 2000.

In an embodiment, a glucose correction dose may be calculated by using Equation 1.

$$\text{Glucose Correction Dose} = (\text{Current G} - \text{Target G}) \times \text{Insulin Sensitivity Factor} \quad \text{Eq. 1}$$

The Glucose Correction Dose may be the amount of insulin needed to adjust the current measured glucose value or concentration to the euglycemic zone. The Current G and Target G may be the current measured glucose value or concentration and the target glucose value or concentration, respectively. The Insulin Sensitivity Factor may be a constant that is special to the user that relates to the proportional effectiveness of insulin.

The insulin bolus amount for carbohydrate coverage dose may be calculated by using Equation 2.

$$\text{Insulin bolus amount for carbohydrate coverage Dose} = \text{Carbohydrate Estimate} \times \text{Insulin-to-Carbohydrate Ratio} \quad \text{Eq. 2}$$

The Carbohydrate Estimate may be the amount consumed by the user and Insulin-to-Carbohydrate Ratio may be a constant that is special to the user relating to the proportional effectiveness of insulin on consumed carbohydrates. A total insulin dose may be calculated by summing together the Glucose Correction Dose and the Carbohydrate Anticipatory Dose.

Under certain circumstances, a user may have trouble determining the correct amount of carbohydrates to input into the bolus calculator. Thus, carbohydrate calculator 500 may be used to help the user covert their food intake into an amount of carbohydrates. The carbohydrate calculator may include a food database that has a wide variety of common foods and the associated nutritional value. The food database may be customized by the user and updated through connecting meter 10 to a computer. A query may be communicated requesting that a user select a food category, sub-food category, food detail, food size, and food quantity, as shown in steps 502, 504, 506, 508, and 510, after the user selects the carbohydrate calculator 500 from the main menu. The food category may include selections such as "bread, pasta, starches," "dairy & eggs," "fruits & vegetables," "meat & fish," and "restaurants." The food category "bread, pasta, starches" may include the following sub-food categories such as bread, pasta, potato, pizza, and other. The sub-food category pizza may include the following food detail such as cheese pizza, pepperoni pizza, Domino's Americano, Domino's Full House, and Pizza Hut Hawaiian. The food detail pepperoni pizza may include the following food size such as small, medium, and large. The food quantity for pepperoni pizza may include the number of servings or slices.

After the user inputs all of the relevant food information (502, 504, 506, 508, 510), a query is communicated asking the user whether another food item needs to be inputted, as shown in a step 512. If the user inputs yes to adding another food item, the carbohydrates calculator goes back to step 502. If the user inputs no to adding another food item, the carbohydrates calculator 500 queries the user whether to calculate an insulin bolus, as shown in a step 514. An output of the carbohydrate estimate and current measured glucose value or concentration may be outputted using the calculate insulin bolus 300 function, if the user selects yes to calculating an insulin bolus. An output of the meal details may be outputted, as shown in a step 518, if the user selects no to calculating an insulin bolus. Meal details may include amount of carbohydrates, carbohydrate choices, calories, cholesterol, total fat, and sodium. Once the user presses an "ok" button, the user interface may go back to the main menu.

Performing a glucose test allows a user to know his/her glucose value or concentration of the user for a particular point in time. However, applicants believe that users have difficulty determining when there is a prudent time period to test again, seek medical assistance, or change insulin therapy based on a high or low glucose reading, a time of eating a meal, a pattern or trend, or a combination thereof. The following will describe a series of methods (600, 700, 800, and 899) for helping users better manage their diabetes disease state by guiding a user to test at an appropriate time and frequency.

Referring back to FIG. 2, the high/low glucose reminder sub-routine 700, the post-meal reminder sub-routine 800, and the pattern and trend analysis sub-routine 899 may be performed subsequent to the glucose test 600. The glucose test 600 may include inserting a biosensor, dosing blood onto the biosensor, and outputting a measured glucose value or concentration, as shown in steps 602, 604, and 606. Next, the user may flag the result as fasting, then the high/low glucose reminder sub-routine 700 may be initiated. In an embodiment, fasting may mean a period of time of greater than about 8 hours to about 10 hours after a meal.

Figure 10A:
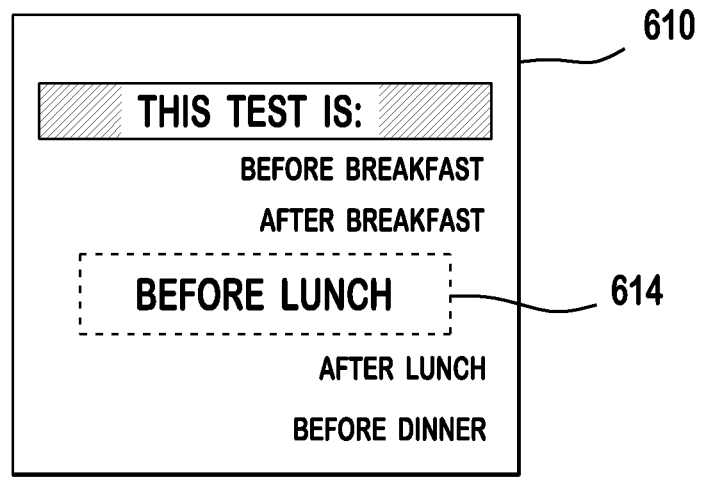
FIG. 10A is a schematic illustrating first screen shots of a user interface where a flag selection "Before Lunch" is highlighted by having an increased font size, according to an exemplary embodiment described and illustrated herein.
Figure 10B:
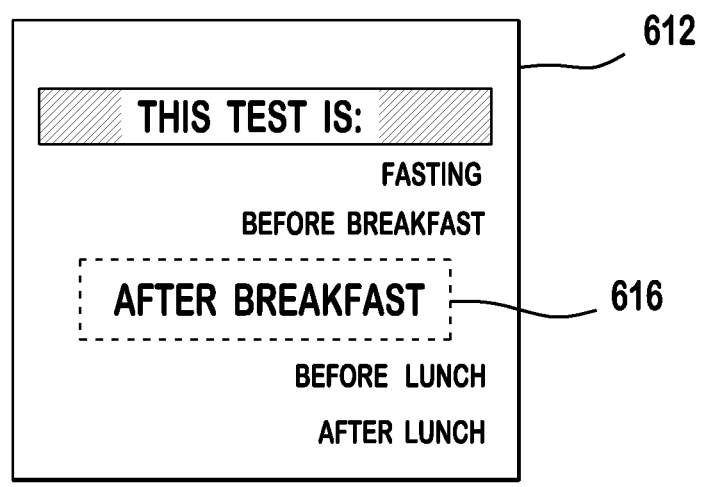
FIG. 10B is a schematic illustrating second screen shots of a user interface where a flag selection "After Breakfast" is highlighted by having an increased font size, according to an exemplary embodiment described and illustrated herein.

A user may be presented with an option to flag the glucose result as fasting to indicate that no food was consumed within a time period before the test. In addition, the user may be given the option to select other types of flags where the glucose measurement is indicated as being after breakfast, before lunch, after lunch, before dinner, after dinner, and night in a simple manner, as illustrated by screen shots 610 and 612 for FIGS. 10A and 10B, respectively. Referring to FIG. 1, the user may press on a second button or a third button (18, 20) to select the type of flag. The process of using second and third button (18, 20) causes the selected flag to appear in a larger font making it easy for the user to determine which flag was selected, as illustrated in FIGS. 10A and 10B. Areas 614 and 616 are examples of selected flags that have an increased font size relative to the unselected flags. Fasting glucose measurements may be a more important indicator of a user's overall diabetes disease state than non-fasting glucose measurements.

Figure 7:
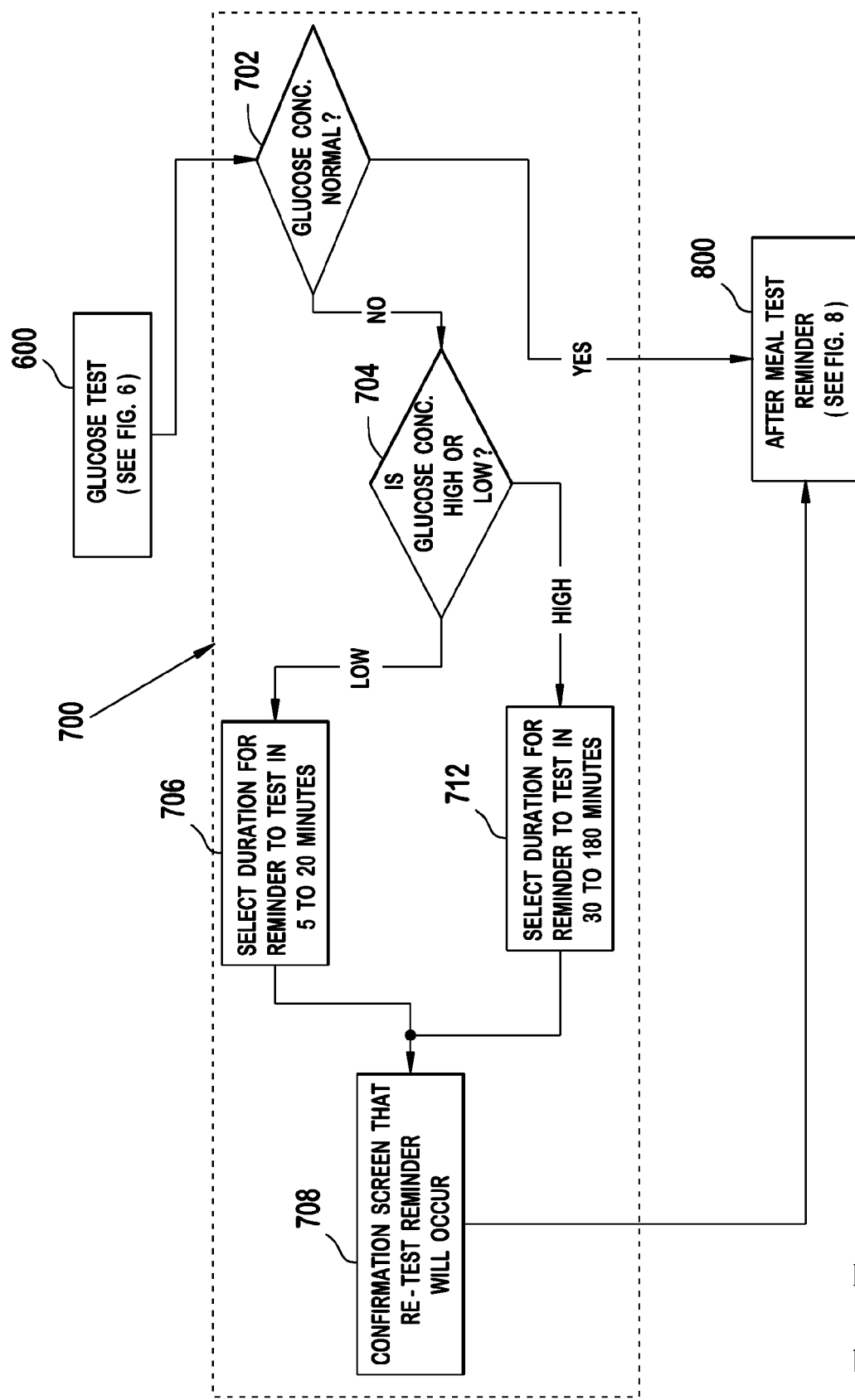
FIG. 7 is a flow chart illustrating an embodiment of a method for performing a high/low glucose reminder sub-routine, according to an exemplary embodiment described and illustrated herein.

FIG. 7 is a flow chart illustrating an embodiment of a method for performing a high/low glucose reminder sub-routine 700. The high/low glucose reminder sub-routine 700 may include determining whether the measured glucose value or concentration is within the euglycemic range (i.e., normal), as shown in a step 702. As a non-limiting example, the euglycemic range may range from about 60-180 mg/dL (or its conversion into mmol/L unit or milliMole per Liter). The high and low thresholds of the euglycemic range may be defined by the user in a high/low glucose reminder setting 900. If the measured glucose value or concentration is not within the euglycemic range, then it is classified as either high or low, as shown in a step 704. A high reading may be a concentration greater than a high threshold and a low reading may be a concentration less than a low threshold. If the measured glucose value or concentration is within the euglycemic range, then the method moves to the after meal test reminder sub-routine 800.

A measured glucose value or concentration lower than the low threshold may prompt the user that the glucose is low and to input a reminder to test within a first retest time period, as shown in a step 706. The first retest time period may range from about 5 minutes to about 30 minutes. A measured glucose value or concentration higher than the high threshold may cause a query to prompt the user to input a reminder to test within a second retest time period, as shown in a step 712. The second retest time period may range from about 30 minutes to about 180 minutes. The second retest time period may be generally greater than the first retest time period because there is usually more urgency in re-testing when the measured glucose value or concentration is low. After either step 706 or 712, a confirmation screen may be shown to the user that a re-test reminder will occur in the future, as shown in a step 708.

Figure 8:
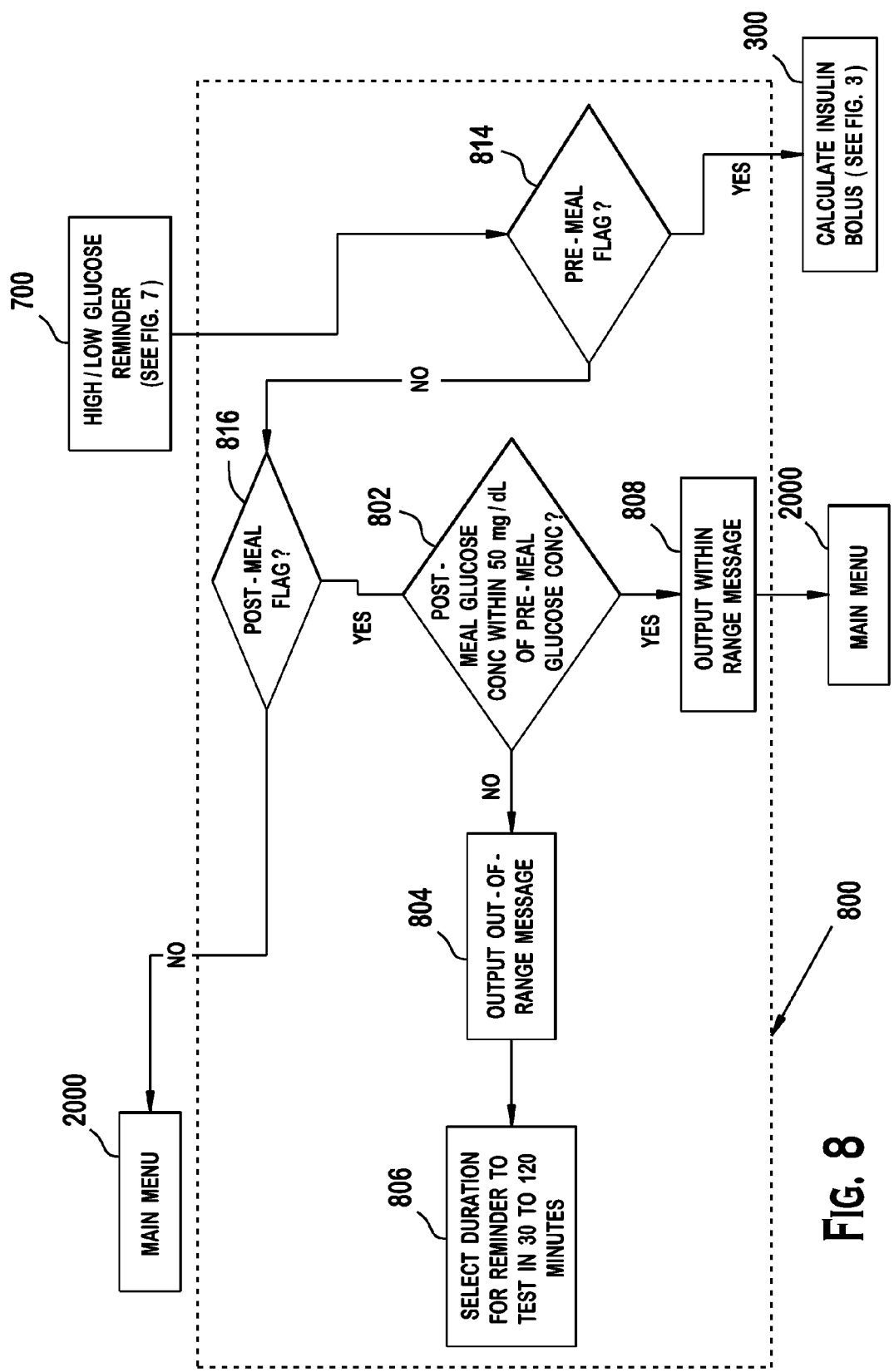
FIG. 8 is a flow chart illustrating an embodiment of a method for performing a post-meal reminder sub-routine, according to an exemplary embodiment described and illustrated herein.

FIG. 8 is a flow chart illustrating an embodiment of a method for performing a post-meal reminder sub-routine 800. The after meal reminder sub-routine 800 includes determining whether the measured glucose value or concentration should be flagged as pre-meal or post-meal, as shown in steps 814 and 816. If the measured glucose value or concentration is flagged as pre-meal, the method should move to the insulin calculator 300. If the measured glucose value or concentration is not flagged as pre-meal or post meal, the method will go back to main menu. If the measured glucose value or concentration is flagged as post-meal, a calculation is performed to determine whether a difference between the post-meal concentration and the pre-meal concentration is within a predetermined range, as shown in a step 802. The predetermined difference range may be about 50 mg/dL (or its conversion into mmol/L unit or milliMole per Liter).

An output message may be communicated notifying the user that the post-meal management of the glucose value or concentration of the user was within the predetermined difference range, as shown in a step 808. The method may then return to main menu 2000 after step 808. A different output message may be communicated notifying the user that the post-meal management of the glucose value or concentration of the user needs improvement if the post-meal glucose value or concentration of the user was not within a predetermined range of the pre-meal glucose value or concentration of the user, as shown in a step 804. Next, a user may be prompted to input a reminder to test within a second retest time period, as shown in a step 806.

Figure 9:
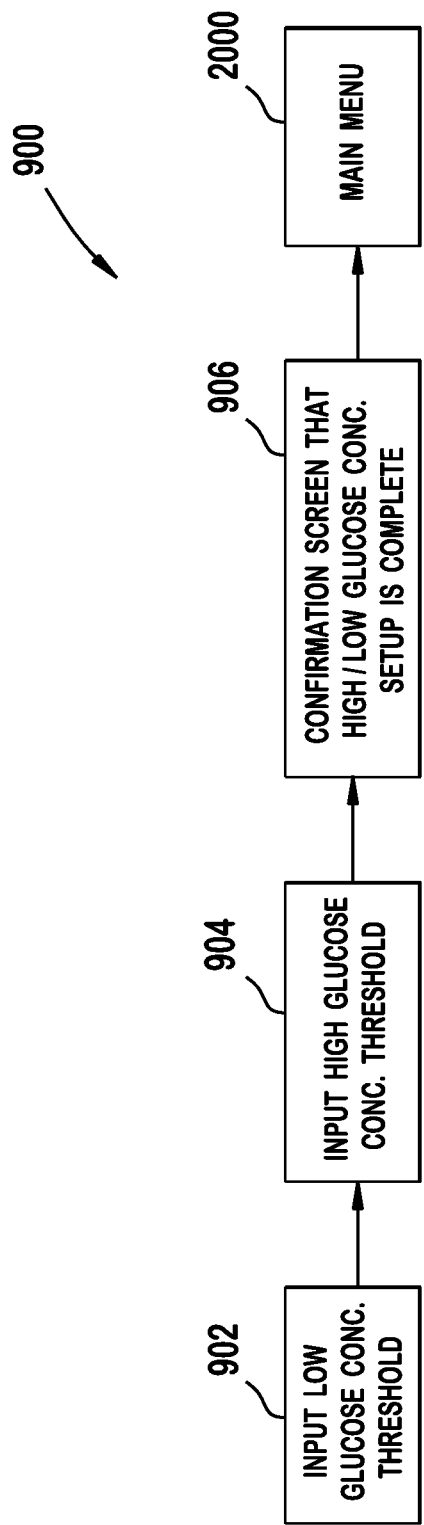
FIG. 9 is a flow chart illustrating an embodiment of a method for setting up the high/low glucose reminder sub-routine, according to an exemplary embodiment described and illustrated herein.

FIG. 9 illustrates a method 900 for configuring the set up of the high/low glucose reminder 800. A user may input a low glucose value or concentration threshold and a high glucose value or concentration threshold, as shown in steps 902 and 904. Next, a confirmation of the high and low glucose value or concentration threshold may be annunciated to the user, as shown in a step 906, which is then followed by returning to main menu 2000.

Pattern and trend analysis sub-routine 899 may be performed to notify a user of their diabetes disease state. A plurality of glucose measurements performed over time may be stored in the meter. By analyzing the trends of the data, meter 10 may provide a warning, recommendation, or tip of an increased likelihood of hyperglycemia occurring in the future. Embodiments suitable for use in the pattern and trend analysis sub-routine may be found in U.S. Provisional application Ser. Nos. 12/052,639, 11/688,639 and U.S. Pre-Grant Publication No. US20080154513, and which are hereby incorporated in whole by reference.

From main menu 2000 of FIG. 2, averages 1000 may be selected, which includes communicating the average glucose value or concentration of the user over a 7, 14, 30, 60, and 90 day period. In addition, averages may also be communicated for the 7 day period, all of the days, fasting, after breakfast, before lunch, after lunch, before dinner, after dinner, night, no answer, and the number of tests performed.

From main menu 2000 of FIG. 2, glucose summary results 1100 may be selected, which includes communicating in a graphical format the highest reading, 30 day average, and lowest reading. Glucose summary results 1100 may also include indicating the proportion of glucose readings above the high threshold, within range, and below the low threshold. Glucose summary results 1100 may also include communicating a histogram indicating the frequency of particular glucose value or concentrations.

From main menu 2000 of FIG. 2, medication reminders 1200 may be selected, which includes allowing a user to input one or more medications into the user interface. The medication reminder may help users remember to take medications. Some users may have trouble memorizing which medications to take and when to take them. In addition, the user may input the amount of medication and the time to take the medication so that an appropriate alarm may be triggered. After taking the medication, the user may confirm the compliance by pressing a button on the user interface.

Figure 6:
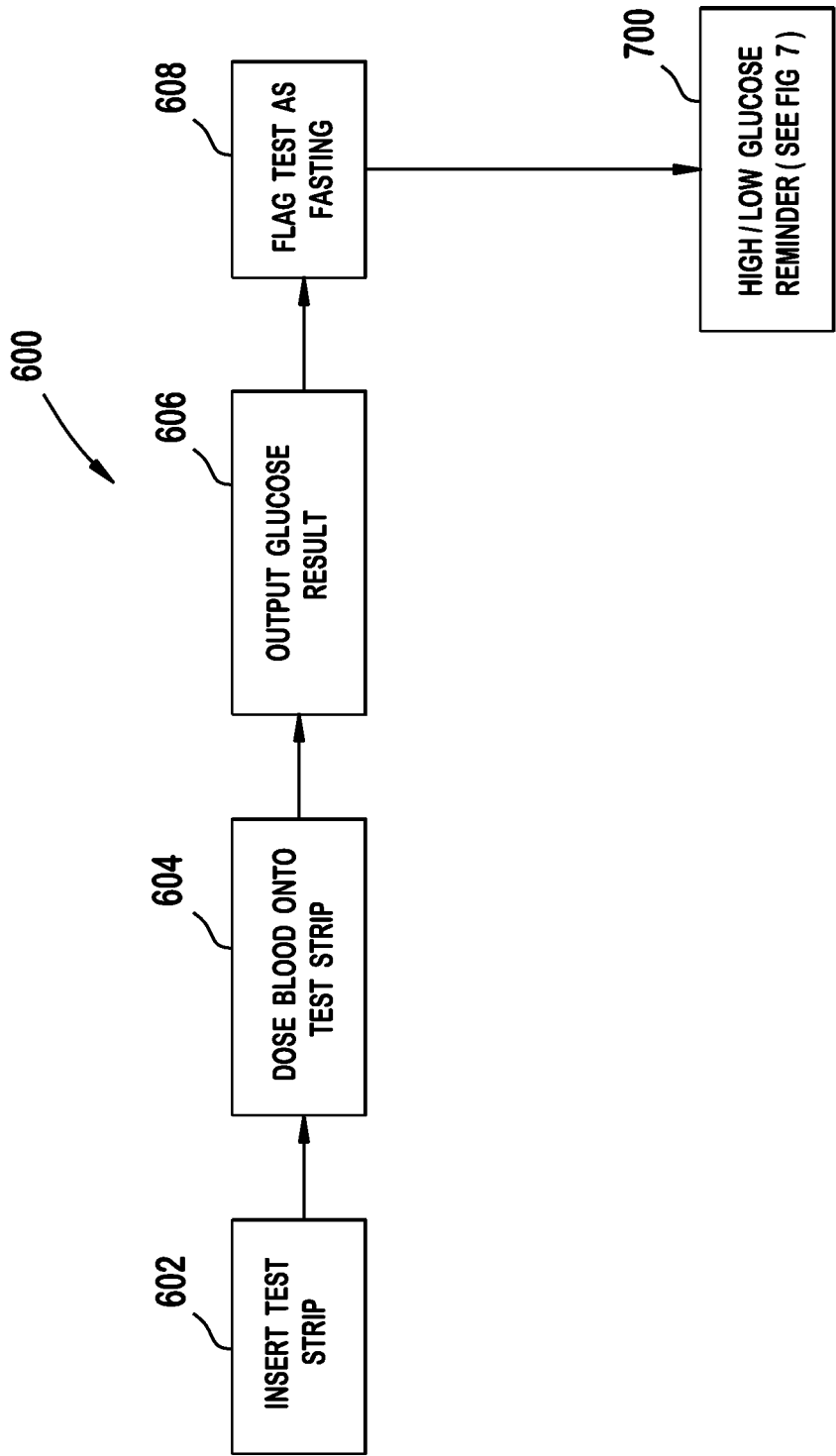
FIG. 6 is a flow chart illustrating an embodiment of a method for performing a glucose test, according to an exemplary embodiment described and illustrated herein.

The following will describe a predictive process that may be implemented for recommending a type of flag before or after outputting a glucose result in step 606 of FIG. 6. An embodiment of a predictive process 690 is illustrated in FIG. 11. Once a type of flag is recommended, the user will have the option of accepting the recommended flag or inputting a different one. Applicants believe that by recommending a correct flag at a high percentage of the time will cause users to flag measurements with a higher degree of compliance because only one button needs to be pressed to accept the recommendation. A user may have to use several button clicks to select a non-recommended flag, which is inconvenient to the user. In an embodiment, a type of flag may be recommended based on the time, the day, and/or past user testing patterns.

Predictive process 690 may be initiated after the output of a glucose value or concentration of the user (step 606). The meter may then perform one of many sub-routines for predicting the type of flag. The sub-routines, which may be performed in the following priority, include "historical data" (steps 620, 626, 630, 624), "schedule," (steps 628, 632, 624) and "default time period" (steps 622, 624).

"Historical data" may use previous glucose readings to suggest a commonly selected flag for a particular time period. For example, if a user had selected the "after dinner" flag at 7 pm multiple times, then the meter will suggest that the same "after dinner" flag for the next reading performed at around 7 pm. In an embodiment, the predictive process may require that at least "n" glucose readings be performed during the same time period with the same type of flag. The minimum number of glucose readings having a matching flag may be adjusted by the user or health care provider. For example, the "historical data" sub-routine may require that three of the last five glucose readings for a particular time period have the same flag type. A time period may be defined as a two hour period, but alternatively may be adjusted by the user or health care provider.

The "historical data" sub-routine may include determining that the measurement was not a first time run, and then reviewing a plurality of past glucose measurements, as shown in steps 620 and 626. Note that "First Time Run" can include the first time that the meter is taken out of its packaging and tested. Next, a determination may be performed to see if there are a suitable number of matching flags for a given time period, as shown in a step 630. If there are a suitable number of matching flags, the meter will then communicate that type of flag, as shown in a step 624. If there are not a suitable number of matching flags, the meter will then go to the "schedule" sub-routine (628, 632, 624).

The "schedule" sub-routine may include determining whether a user had previously inputted a mealtime schedule, as shown in a step 628. If there is an inputted mealtime schedule, then the meter may find the corresponding flag type based on the time that the glucose measurement was performed, as shown in a step 632. Next, the meter may communicate the type of flag, as shown in step 624. If the inputted mealtime schedule has not been entered, then the meter will go to the "default time period" sub-routine (622, 624).

The "default time period" sub-routine may include a set of time periods in which the meter would suggest a type of meal flag to the user for a particular time period of the day. The set of time periods may be saved to the meter memory at the time of manufacture. Thus, if the user has not previously inputted a personal mealtime schedule, then the meter will recommend meal flags based on the default time periods stored in the meter memory. In addition, if the meter determines that the glucose measurement is the first measurement of the day (step 620), then the meter will recommend a type of flag based on the default time period (step 622).

Once the user is presented with the recommended type of flag, the user has the option to override the suggestion, as shown in a step 634. If the user accepts the recommendation, the type of flag and measurement time are stored in the meter memory, as shown in a step 638. If the user overrides the suggestion, the user selects a type of flag, as shown in a step 636, and then the type of flag and measurement time are stored in the meter memory, as shown in step 638.

After storing the type of flag and measurement time, the meter will determine whether the glucose measurement was a first time run, as shown in a step 640. If the glucose measurement was a first time run, then the meter will offset all of the mealtime measurements, as shown in a step 644. After the offset step, the meter will communicate the glucose result with the associated flag, as shown in a step 648.

If the glucose measurement was not a first time run, then the meter will check the last five glucose readings having the same type of flag, as shown in a step 642. Next, the meter determines whether the time for the most recent flag differs by more than two hours from the last five glucose readings, as shown in a step 646. If the most recent flag differs by more than two hours from each of the last five glucose readings, then the meter will offset all of the meal time measurements, as shown in step 644. If the most recent flag does not differ by more than two hours from each of the last five glucose readings or if at least five glucose measurements having a particular type of flag have not been saved to memory, then the will simply communicate the glucose result with the associated flag, as shown in a step 648. The following will describe an example of applying an offset. Initially, before a first time run, the initial profile values can be Fasting: 08:00, After Breakfast: 10:00, Before Lunch: 13:00, After Lunch: 15:00, Before Dinner: 18:00, After Dinner: 20:00, Before Bed: 22:00, and Nighttime: 23:00. As an example, a user can run a glucose test at 15:00 where the meter will suggest a Before Lunch flag. However, if the user changes this value to be Fasting, then this is a difference of 7 hours (15:00-8:00) and therefore greater than the 2 hour threshold. As a result, the system would then shift the profile values to be Fasting: 15:00, After Breakfast: 17:00, Before Lunch: 20:00, After Lunch: 22:00, Before Dinner: 01:00, After Dinner: 03:00, Before Bed: 05:00, Nighttime: 06:00.

Now that user interface 2001 has been described, the following will describe glucose meter 10, insulin pen 28, and insulin pump 48. Referring back to FIG. 1, glucose meter 10 may include a housing 11, user interface buttons (16, 18, 20), a communication output unit in the form of a display 14, a biosensor port connector 22, and a data port 13. User interface buttons (16, 18, and 20) may be configured to allow the entry of data, navigation of menus, and execution of commands. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual. Specifically, user interface buttons (16, 18, 20) include a first user interface button 16, a second user interface button 18, and a third user interface button 20. User interface buttons (16, 18, 20) include a first marking 17, a second marking 19, and a third marking 21, respectively, which allow a user to navigate through the user interface. It should be noted that the user interface buttons include not only physical buttons but also virtual buttons provided in the form of icons on a touch screen type interface.

Figure 12:
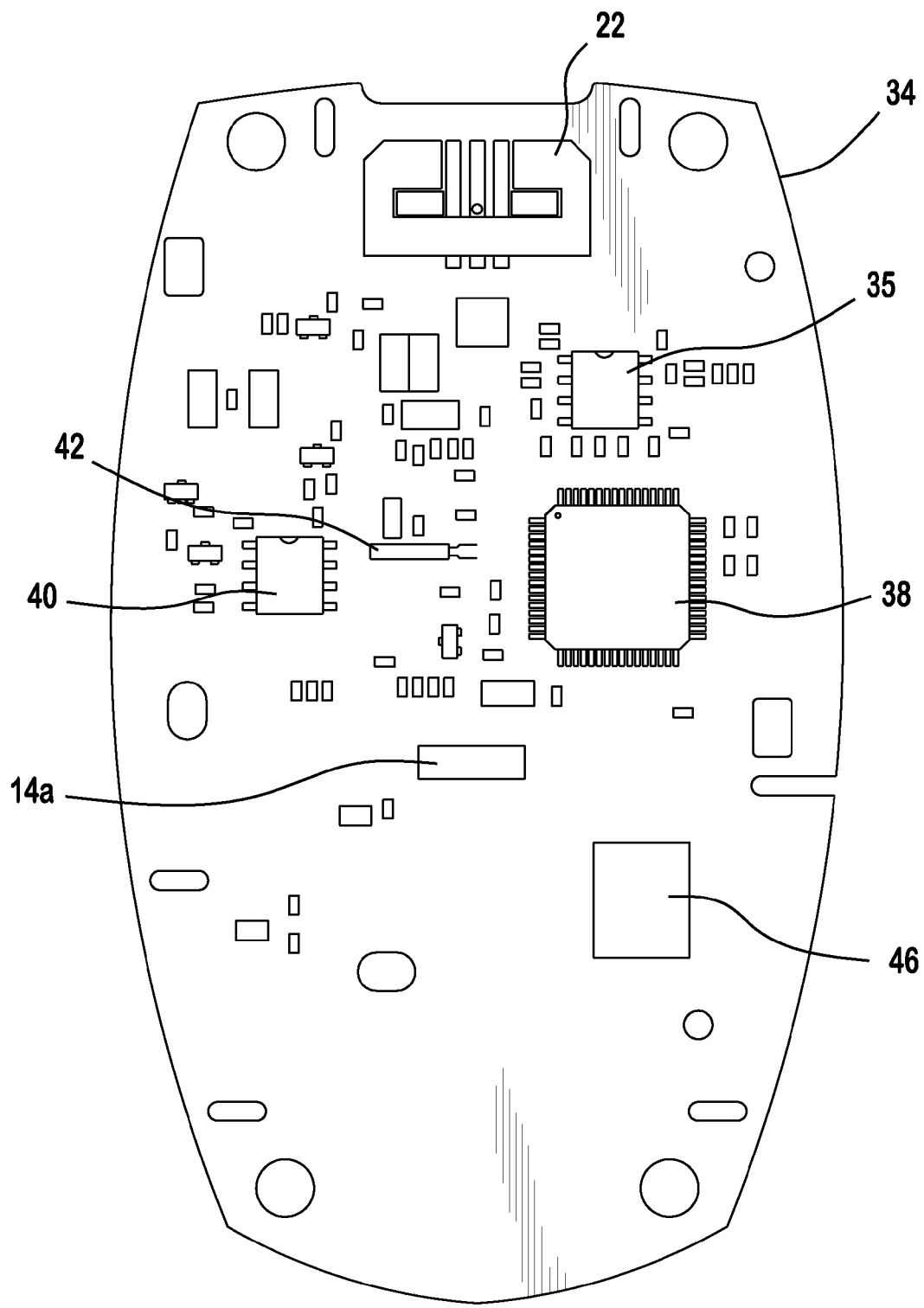
FIG. 12 illustrates a top portion of a circuit board of the analyte measurement and management device of FIG. 1, according to an exemplary embodiment described and illustrated herein.
Figure 13:
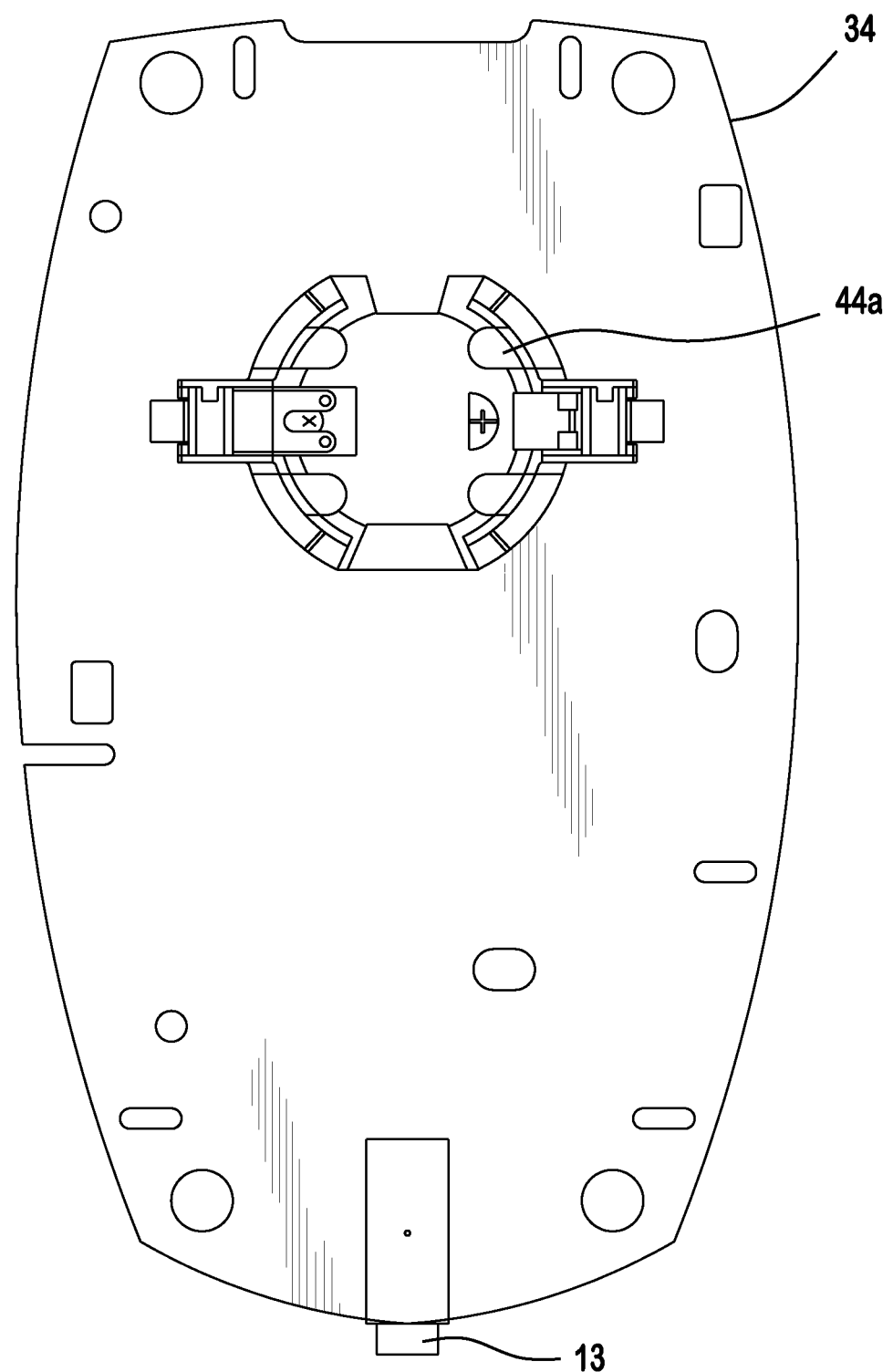
FIG. 13 illustrates a bottom portion of the circuit board of the analyte measurement and management device of FIG. 1, according to an exemplary embodiment described and illustrated herein.

The electronic components of meter 10 may be disposed on a circuit board 34 that is within housing 11. FIGS. 12 and 13 illustrate the electronic components disposed on a top surface and a bottom surface of circuit board 34, respectively. On the top surface, the electronic components include a biosensor port connector 22, an operational amplifier circuit 35, a microcontroller or processor 38, a communication output connector 14a, a non-volatile memory 40, a clock 42, and a first wireless module 46. On the bottom surface, the electronic components include a battery connector 44a and a data port 13. Processor 38 may be electrically connected to biosensor port connector 22, operational amplifier circuit 35, first wireless module 46, communication output 14, non-volatile memory 40, clock 42, battery connector 344a, data port 13, and user interface buttons (16, 18, and 20).

Operational amplifier circuit 35 may be two or more operational amplifiers configured to provide a portion of the potentiostat function and the current measurement function. The potentiostat function may refer to the application of a test voltage between at least two electrodes of a biosensor. The current function may refer to the measurement of a test current resulting from the applied test voltage. The current measurement may be performed with a current-to-voltage converter. Processor 38 may be in the form of a mixed signal microprocessor (MSP) such as, for example, the Texas Instrument MSP 430. The MSP 430 may be configured to also perform a portion of the potentiostat function and the current measurement function. In addition, the MSP 430 may also include volatile and non-volatile memory. In another embodiment, many of the electronic components may be integrated with the processor in the form of an application specific integrated circuit (ASIC).

Biosensor port connector 22 may be configured to form an electrical connection to the biosensor. Communication output connector 14a may be configured to attach to communication output 14. Communication output 14 may be in the form of a liquid crystal display for reporting measured glucose levels, and for facilitating entry of lifestyle related information. Communication output 14 may alternatively include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured for measuring time and be in the form of an oscillating crystal. Battery connector 44a may be configured to be electrically connected to a power supply.

In an embodiment, biosensor 24 may be in the form of an electrochemical glucose test strip. Test strip 24 may include one or more working electrodes and a counter electrode. Test strip 24 may also include a plurality of electrical contact pads, where each electrode is in electrical communication with at least one electrical contact pad. Biosensor port connector 22 may be configured to electrically interface to the electrical contact pads and form electrical communication with the electrodes. Test strip 24 may include a reagent layer that is disposed over at least one electrode. The reagent layer may include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer may be configured to physically transform glucose into an enzymatic by-product and in the process generate an amount of reduced mediator (e.g., ferrocyanide) that is proportional approximately to the glucose value or concentration present in a physiological fluid of the user or in the user's blood. The working electrode may then measure a concentration of the reduced mediator in the form of a current. In turn, glucose meter 10 may convert the current's magnitude into a glucose value or concentration of the user.

Referring back to FIG. 1, the second component of the diabetes management system may include a therapeutic agent delivery device 28, which has a housing, preferably elongated and of sufficient size to be handled by a human hand comfortably. The device 28, which may be referred to as an insulin pen, is provided with electronic module 30 to record dosage amounts delivered by the user, as illustrated in FIG. 1. The device 28 may include a second wireless module 32 disposed in the housing that, automatically without prompting from a user, transmits a signal to the first wireless module of glucose meter 10. The wireless signal may include data to (a) type of therapeutic agent delivered; (b) amount of therapeutic agent delivered to the user; or (c) time or date of therapeutic agent delivered and combinations of (a)-(c).

In an embodiment, a therapeutic delivery devices may be in the form of a "user-activated" therapeutic delivery device, which requires a manual interaction between the device and a user (for example, by a user pushing a button on the device) to initiate a single therapeutic agent delivery event and that in the absence of such manual interaction deliver no therapeutic agent to the user. A non-limiting example of such a user-activated therapeutic agent delivery device is described in U.S. Provisional Application No. 61/040,024 now U.S. application Ser. No. 12/407,173 filed on 19 Mar. 2009; U.S. application Ser. No. 12/417,875 filed on Apr. 3, 2009; U.S. application Ser. No. 12/505,007 and entitled "Analyte Measurement and Management Device and Associated Methods,"), filed on Jul. 17, 2009, each of which is hereby incorporated in whole by reference. Insulin pens are loaded with a vial or cartridge of insulin, and are attached to a disposable needle. Portions of the insulin pen may be reusable, or the insulin pen may be completely disposable. Insulin pens are commercially available from companies such as Novo Nordisk, Aventis, and Eli Lilly, and may be used with a variety of insulin, such as Novolog, Humalog, Levemir, and Lantus. U.S. Patent Application Publication No. 2005/0182358 illustrates an exemplary insulin pen with activation of an algorithm upon removal of the insulin pen from a carrying case. U.S. Patent Application Publication No. 2005/0182358 is hereby incorporated by reference into this application.

The third component may be a health care provider's ("HCP's") computer 26 which may be used to communicate with the analyte measurement device and/or the delivery device. In one example, the computer 26 may be connected via a mobile network to the device 10 or 28. Alternatively, the computer 26 may be connected for communication via a short-range wireless network such as, for example, infrared, Bluetooth or WiFi. In the system shown exemplarily, computer 26 may be located remotely in a diabetes clinic or hospital so that certain therapeutic protocols, which have been customized for a particular diabetic user's physiological requirements, may be transferred to such a user remotely. A personal computer, running appropriate software, allows entry and modification of set-up information (e.g. the current time, date, and language), and may perform analysis of data collected by analyte measurement device 10. In addition, the personal computer may be able to perform advanced analysis functions, and/or transmit data to other computers (i.e. over the internet) for improved diagnosis and treatment. Connecting analyte measurement device 10 with a local or remote computer may facilitate improved treatment by health care providers.

Figure 14:
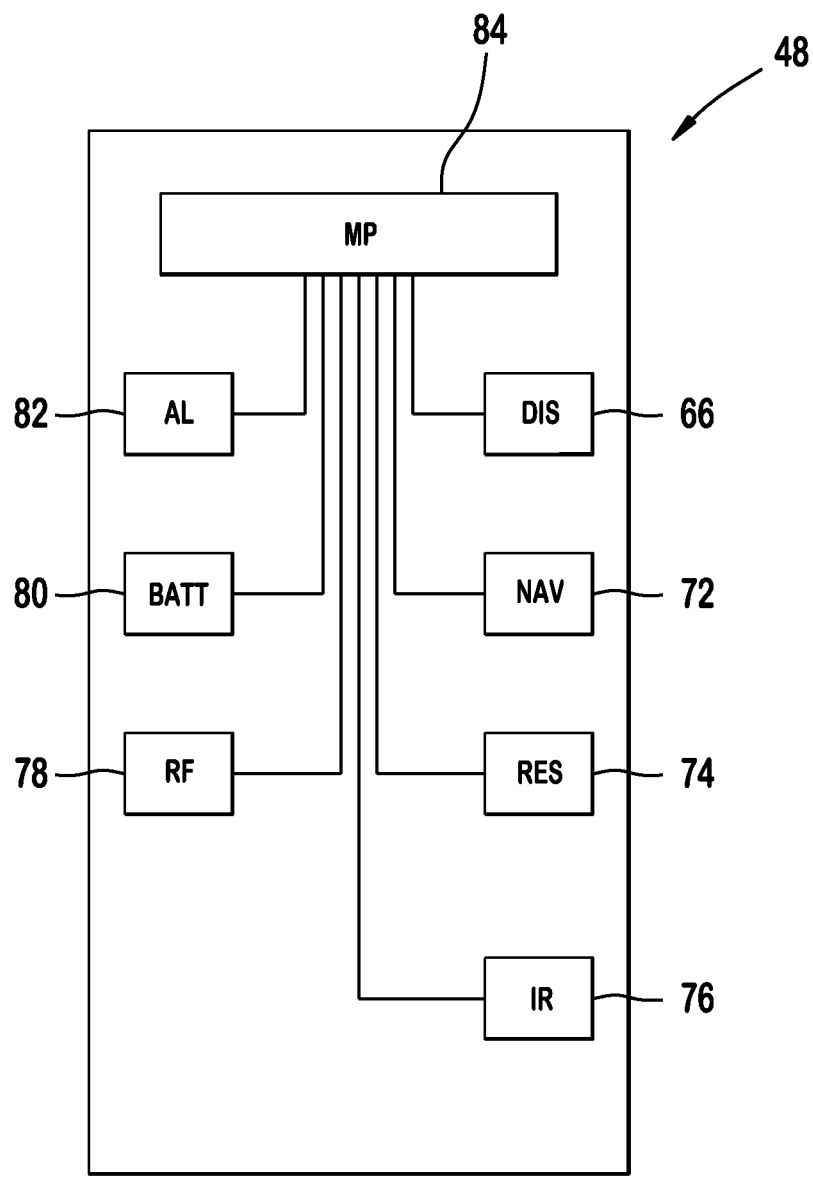
FIG. 14 illustrates a schematic of the functional components of an insulin pump, according to an exemplary embodiment described and illustrated herein.

Referring to back to FIG. 1, a therapeutic dosing device may also be a pump 48 that includes a housing 50, a backlight button 52, an up button 54, a cartridge cap 56, a bolus button 58, a down button 60, a battery cap 62, an OK button 64, and a communication output 66. Pump 48 may be configured to dispense medication such as, for example, insulin for regulating glucose levels. Pump 48 may be similar to a commercially available pump from Animas, Corp. (West Chester, Pa., Catalog No. IR 1200). FIG. 14 illustrates a schematic of the functional components of insulin pump 48, which includes a communication output (DIS) 66, navigational buttons (NAV) 72, a reservoir (RES) 74, an infrared communication port (IR) 76, a radio frequency module (RF) 78, a battery (BAT) 80, an alarm module (AL) 82, and a microprocessor (MP) 84. Note that navigational buttons 72 may include up button 54, down button 60, and ok button 64.

By virtue of the analyte and data management device 10 described above, the device 10 may be programmed with instructions to carry out the various methods described herein. In one embodiment, the device 10 may include a housing 11 that has a biosensor port 22 coupled to an analyte measurement unit 35 to provide data regarding an amount of glucose measured in a user's physiological fluid deposited on the test strip 24. The device 10 also includes a communication output unit coupled to a processor 38 with a plurality of user interface buttons 16, 17, and 18. The processor 38 is coupled to the analyte measurement unit 35, a memory, user interface buttons, and the communication output. The processor 38 is programmed to: verify whether a most recent glucose measurement was made within a first predetermined time period; based on the user's selection, recommend an insulin bolus amount for (1) glucose correction only; (2) carbohydrate coverage only; or (3) both carbohydrate and glucose correction; and annunciate the insulin bolus recommendation. The processor may also be programmed to verify whether a most recent glucose measurement was made within a first predetermined time period; query the user as to whether an insulin calculation was utilized by the user in the last 3 hours and if true, warn the user that insulin may still be physiologically active to the user in a situation during which the user took insulin; and recommend an insulin bolus based on both carbohydrate coverage and glucose correction. In another embodiment, the last 3 hour time period may be increased to about 3 to about 5 hours.

Alternatively, the processor may also be programmed to: verify whether a most recent glucose measurement was made within a first predetermined time period; query the user as to whether an insulin calculation was utilized by the user in the last 3 hours and if true, warning the user that insulin may still be physiologically active to the user in a situation during which the user took insulin; and recommend an insulin bolus based on both carbohydrate coverage and glucose correction. In another embodiment, the last 3 hour time period may be increased to about 3 to about 5 hours.

In a further variation, the processor may be programmed to: verify whether a most recent glucose measurement was made within a first predetermined time period; determine an insulin bolus for delivery to the user based on at least one of the plurality of blood glucose measurement values, insulin sensitivity of the user, insulin to carbohydrate ratio, and target glucose value; and remind the user to conduct a glucose measurement within a second predetermined time period whenever a glucose measurement from the user's physiological fluid indicates an abnormal glucose value. The second predetermined time period may range from about 5 minutes to about 180 minutes. A sub-set of the second predetermined time period may be referred to as a first retest time period or a second retest time period.

In yet another variation, the processor may be programmed to: flag a glucose measurement conducted by the user as a fasting glucose measurement; in the event the flagged fasting glucose measurement is less than a first threshold, remind the user to conduct another glucose measurement after a first retest time period; in the event the flagged fasting glucose measurement is greater than a second threshold, remind the user to conduct another glucose measurement after a second retest time period. In yet a further variation, the processor may be programmed to: flag the before meal glucose measurement in the memory of the analyte measurement and management device 10 as a pre-meal glucose value; flag an after-meal glucose measurement in the memory of the analyte measurement and management device 10 as a post-meal value; determine whether a difference between the flagged post-meal glucose value and flagged pre-meal glucose value is within about 50 mg/dL; notify the user whenever the difference is greater than about 50 mg/dL; and remind the user to re-test in a second retest time period.

It should be noted that the methods or processors described herein are not limited to implementation in the analyte and data management unit 10 but may also be implemented with other health monitoring devices. For example, a processor in a mobile phone may be programmed as described earlier to work with blood glucose data received from a separate glucose meter (e.g., biosensor type meter or continuous glucose monitor). Alternatively, a processor in the insulin pump 50 may also be programmed as described earlier to work with blood glucose data received from a glucose test strip meter or a continuous glucose monitoring device. In the same spirit, a processor in the insulin pen 28 may also be programmed with the exemplary methods to work with blood glucose data received from a glucose test strip meter or a continuous glucose monitoring device.

As noted earlier, the microprocessor can be programmed to generally carry out the steps of various processes described herein. The microprocessor can be part of a particular device, such as, for example, a glucose meter, an insulin pen, an insulin pump, a server, a mobile phone, personal computer, or mobile hand held device. Furthermore, the various methods described herein can be used to generate software codes using off-the-shelf software development tools such as, for example, C, C+, C++, C-Sharp, Visual Studio 6.0, Windows 2000 Server, and SQL Server 2000. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microprocessor or computer, are operable to carry out the steps described in these methods along with any other necessary steps.

While preferred embodiments of the present invention have been shown and described herein, it will be obvious to those skilled in the art that such embodiments are provided by way of example only. For example, the invention may be applied not only to docking stations and glucose meters, but may also be applied to any electronic device that needs a power supply and that may be re-set such as insulin infusion pump, continuous glucose monitoring system and the like. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. A method of managing blood glucose value of a diabetes user with a glucose measurement unit and a data management unit, each of the glucose measurement unit and the data management unit having respective processors, the method comprising:

conducting a plurality of glucose measurements from physiological fluids of a user with the glucose measurement unit that is coupled to a data management unit whereby glucose in the fluids is transformed into enzymatic byproducts during the measurements;

verifying with one of the glucose measurement unit and the data management unit, whether a most recent glucose measurement was made within a first predetermined time period different from a second predetermined time period which is different from a third predetermined time period;

based on the user's selection of an estimation of carbohydrates or calculation carbohydrates, recommending an insulin bolus amount for (a) glucose correction only; (b) carbohydrate coverage only; or (c) both carbohydrate coverage and glucose correction, the recommending comprises:

verifying with one processor of either the glucose measurement unit or the data management unit, whether an insulin bolus amount for glucose correction was entered by the user within the third predetermined time period and if true then (a) warning the user that insulin may still be physiologically active to the user in a situation during which the user took insulin; and (b) recommending an insulin amount for carbohydrate coverage only otherwise determining:

(1) whether a pre-meal flag is set with a glucose measurement conducted within the third predetermined time period and if true then (i) warning the user that insulin may still be physiologically active to the user in a situation during which the user took insulin; and (ii) recommending an insulin amount for carbohydrate coverage, otherwise if not true then (2) whether a latest glucose measurement is flagged as post-meal within the third predetermined time period and if true then (i) warning the user that insulin may still be physiologically active to the user in a situation during which the user took insulin; and (ii) recommending an insulin amount for carbohydrate coverage with a warning that a full bolus calculation should be used with pre-meal glucose concentration; and annunciating with the one processor, the insulin bolus recommendation; treating the user with the insulin bolus recommendation.

2. The method of claim 1, in which each of the recommending of the insulin bolus amount for each one of (a) glucose correction only; (b) carbohydrate coverage only; or(c) both carbohydrate coverage and glucose correction comprises:

inputting an amount of carbohydrate to be ingested by the user; and calculating the insulin bolus amount based on an insulin sensitivity of the user, insulin to carbohydrate ratio, and a target glucose value.

3. The method of claim 2 wherein the step of recommending further includes a recommendation of a default amount of carbohydrate to the user ranging from about 30 grams to about 50 grams.

4. The method of claim 3, in which the third predetermined time period comprises any value from about 3 hours to about 5 hours.

* * * * *